United States Patent
Fofonoff et al.

[11] Patent Number: 5,882,929
[45] Date of Patent: Mar. 16, 1999

[54] METHODS AND APPARATUS FOR THE CONDITIONING OF CARTILAGE REPLACEMENT TISSUE

[75] Inventors: Timothy W. Fofonoff, Dedham; Eugene Bell, Boston, both of Mass.

[73] Assignee: Tissue Engineering, Inc., Boston, Mass.

[21] Appl. No.: 56,675

[22] Filed: Apr. 7, 1998

[51] Int. Cl.$^6$ .............................. C07C 00/00; C12M 3/00
[52] U.S. Cl. .................. 435/395; 435/284.1; 435/286.5; 600/36; 73/790; 73/807; 73/818; 73/843; 73/846; 73/847
[58] Field of Search ............................... 435/1.1, 1.2, 395, 435/402, 283.1, 284.1, 286.5; 600/36; 606/57; 73/788, 790, 813, 814, 818, 841, 843, 846, 847, 807

[56] References Cited

U.S. PATENT DOCUMENTS

| | | | |
|---|---|---|---|
| 5,521,087 | 5/1996 | Lee et al. | 435/240.2 |
| 5,700,688 | 12/1997 | Lee et al. | 435/287.1 |
| 5,792,603 | 8/1998 | Dunkelman et al. | 435/1.2 |

OTHER PUBLICATIONS

D. Huang et al., "Mechanisms and Dynamics of Mechanical Strengthening in Ligament–Equivalent Fibroblast–Populated Collagen Matrices," *Annals of Biomedical Engineering*, vol. 21, pp. 289–305 (1993).

E. Bell, *Tissue Engineering: Current Perspectives*, Birkhäuser, Boston, 1993.

*Primary Examiner*—David A. Redding
*Attorney, Agent, or Firm*—Lahive & Cockfield, LLP; Anthony A. Laurentano

[57] ABSTRACT

Apparatus and methods are disclosed for maturing a biopolymer tissue construct in vitro prior to use as a replacement construct in vivo as, for example, a graft, implant, or prosthesis. The tissue is seeded with specific cells, exposed to a maturation fluid, such as a synovial-like fluid containing hyaluronic acid, and subjected to selected conditioning and maturation forces, which can include frictional forces, shear forces, and compressive pressure. The tissue is mounted on a first support element and a second surface applies a selected force to the tissue. This maturation process occurs within a maturation chamber. The resultant matured replacement tissue construct is intended to provide a replacement tissue that is more readily integrable in vivo to produce a more durable and functional replacement tissue.

86 Claims, 9 Drawing Sheets

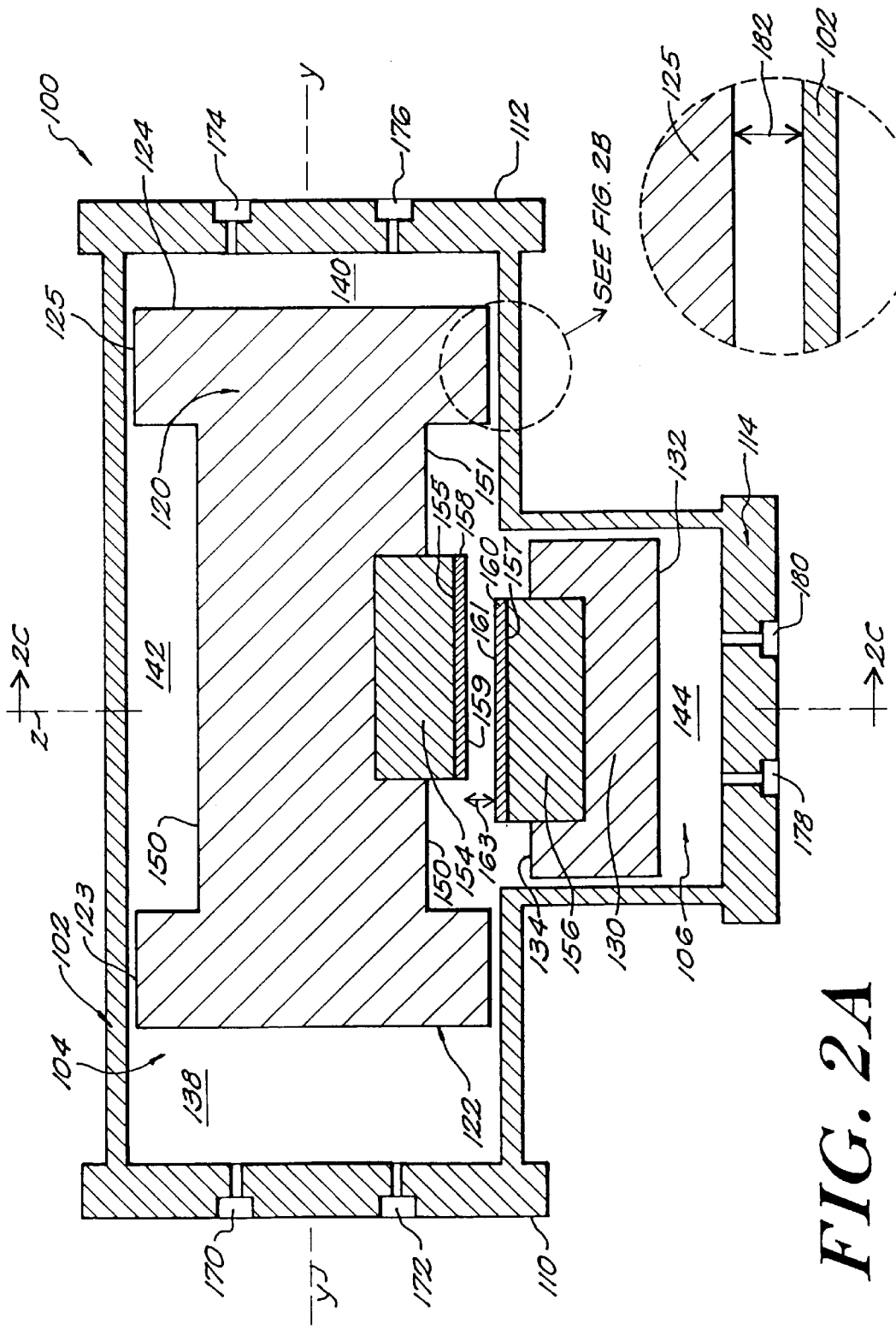

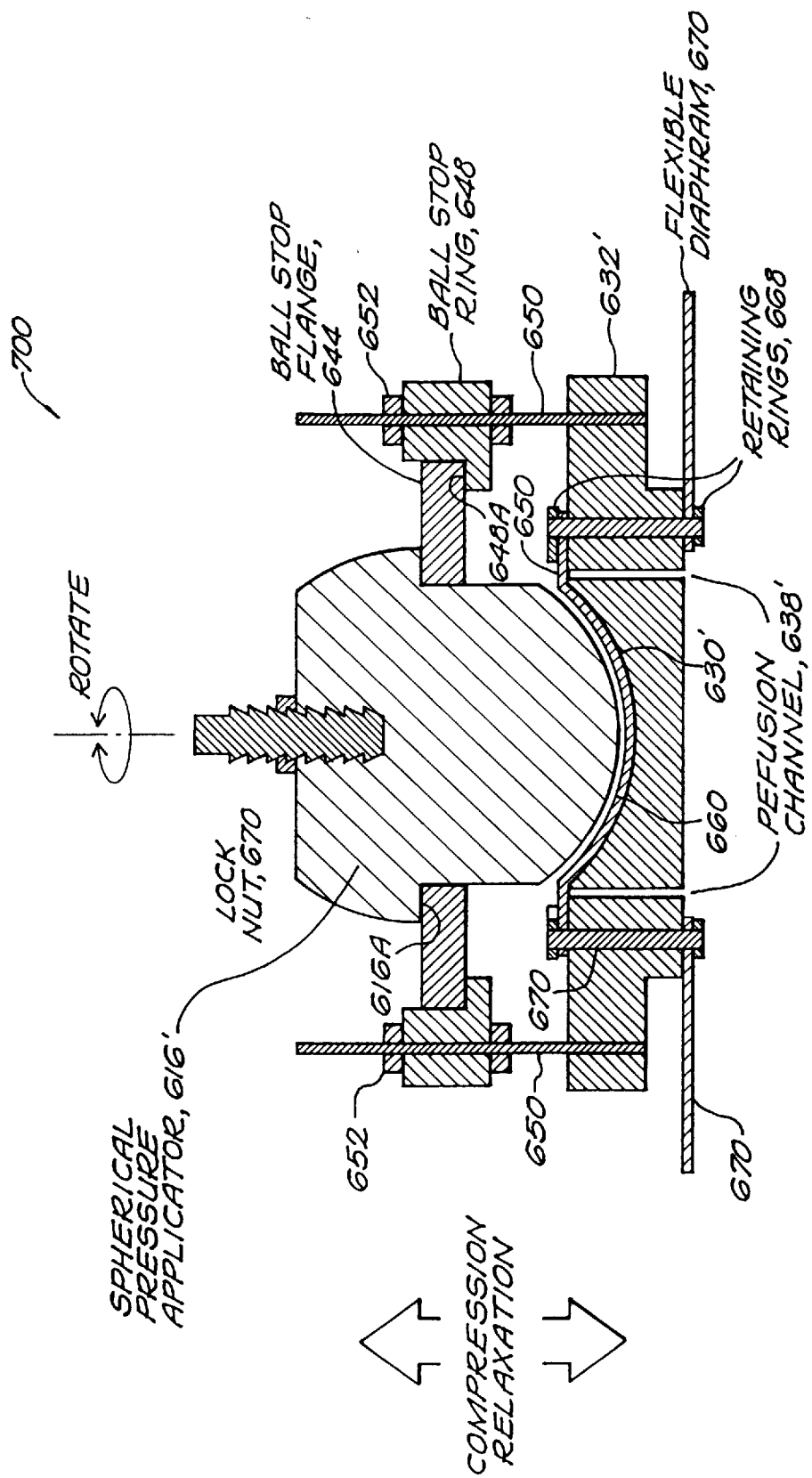

METHODS AND APPARATUS FOR THE CONDITIONING OF CARTILAGE REPLACEMENT TISSUE

BACKGROUND OF THE INVENTION

This application relates to the preparation of grafts, implants, prostheses or other tissue constructs, typically for use as replacements for damaged or diseased bodily tissue. More particularly, this application relates to the maturation, or conditioning, of biopolymer tissue constructs prior to implantation of the construct in the body.

Tissue constructs are often used as grafts, implants or prostheses to replace diseased or damaged bodily tissue. Tissue needing replacement can include, for example, cartilage, tendon and ligament tissue. A fully functional replacement tissue should withstand at least the stresses and strains imposed by normal bodily activity on the type of tissue the construct is to replace. Furthermore, the construct should be biocompatible and integrable, in vivo, i.e., the construct should resemble a natural tissue so as to attract and interact with specific cells present in the body. The attracted cells further organize the construct and secrete specific biosynthetic products, such as extracellular matrix proteins and/or growth factors, that bind to the replacement construct, enabling it to degrade, remodel and regenerate as a fully functional replacement tissue. Such integration strengthens and conditions the construct to better perform as a replacement tissue.

Synthetic materials such as polyester fibers (Dacron™) or polytetrafluoroethylene (PTFE) (Teflon™) have been used extensively as replacements for bodily tissue, with some success. However, due to the poor biocompatibility of such synthetic materials, they often initiate persistent inflammatory reactions. Additionally, they do not readily breakdown and are not readily integrated with the body via remodeling by tissue cells.

It is also known to fabricate replacement constructs from structural biopolymer matrix components, such as collagen, that are extracted, purified and combined with specialized cells. The cells can organize, condense, and otherwise interact with the matrix proteins to create a tissue-like construct that can more closely resemble a natural tissue, and hence more readily integrate with the body than implants, grafts or prostheses based on synthetic materials. However, available biopolymer implants do not always have, or develop in vivo, the matrix complexity characteristic of the tissue they are to replace so as to become fully-functional replacements.

Therefore, there is a need for improved replacement tissue constructs that are stronger and more readily integrable with the bodily environment.

Accordingly, one object of the invention is to provide methods and apparatus for producing improved replacement tissue constructs.

Another object of the invention is to provide replacement tissue constructs that are stronger and more capable of withstanding the stresses and strains imposed thereon by the rigors of bodily activity.

A further object of the invention is to provide prostheses, grafts and implants that are more readily accepted by and integrable with the natural bodily environment.

Another object of the invention is to provide prostheses, grafts and implants that more readily resemble the tissues they are intended to replace.

Other objects and advantages of the present invention will be appreciated by one of ordinarily skill in the art from the following disclosure, including the drawings and the claims.

The invention will next be described in connection with various preferred embodiments. However, it should be clear that various changes and modifications can be made by those skilled in the art without departing from the spirit and scope of the invention.

SUMMARY OF THE INVENTION

The present invention attains the foregoing and other objects by providing methods and apparatus for exposing biopolymer replacement tissue or tissue constructs to selected conditions, i.e., to a selected maturation fluid and to selected forces and/or stresses, for maturing the replacement tissue prior to insertion of the tissue into the body.

As used herein, maturing a tissue refers to conditioning a tissue such that it is more integrable with the bodily environment. Hence, an integrable tissue is a tissue that more readily remodels, degrades and regenerates, within the body, to create a stronger and more durable functional replacement tissue.

As used herein, a biopolymer is a polymer suitable for introduction into a living organism, e.g., a human. The biopolymer is usually non-toxic and bioabsorbable when introduced into the living organism, and any degradation products of the biopolymer are also non-toxic to the organism. The biopolymer can be formed into biocompatible constructs that include, for example, biopolymer foams, e.g., single or double density foams, and/or biopolymer fibers. A typical biopolymer is collagen.

Typically, biopolymer tissue to be matured using the apparatus and methods of the present invention is seeded with cells, such as chondrocyte cells obtained from a biopsy of human or animal tissue. Exposing the replacement tissue to maturation fluid and subjecting the tissue to selected forces is considered to provide an environment that, similar to the natural bodily environment, provides biological signals to the seed cells for producing an integrable replacement tissue more readily accepted by the body. For example, the biological signals provided by the methods and apparatus of the present invention may promote, in addition to other beneficial effects, the secretion of extracellular matrix material, the generation of cell binding sites that attract specific cells from the body and/or cell differentiation.

A useful maturation fluid is a thixotropic, synovial-like fluid that transmits shear forces to the biopolymer tissue as a result of relative motion between the tissue surface and a second surface that faces the tissue surface, and which is spaced therefrom. The selected forces and/or stresses imposed upon the tissue can include shear forces, frictional forces, torsional forces and compressive forces. The invention is intended to be particularly useful for the maturation of replacement cartilage tissue.

According to one aspect, the invention provides an apparatus that includes a first support element having a first surface for receiving and mounting a biopolymer tissue and a second support element having a second surface facing a surface of the biopolymer tissue. The first and second surfaces can be spaced apart to form a gap. Also included are a fluid element, such as reservoir, for introducing a maturation fluid to the tissue received by the first surface and to the second surface, and a relative motion element coupled to one or both of the first and second support elements for providing relative motion between the first and second surfaces. The relative motion subjects the tissue to selected forces, such as shear forces transmitted by the maturation fluid, or direct frictional forces due to contact of the first tissue surface and the second surface of the second support element. The fluid element typically confines the maturation fluid and maintains the fluid in communication with the biopolymer tissue received and mounted by the first surface, such as by immersing the two surfaces in the maturation fluid and filling any gap therebetween with fluid. The fluid element, however, need not be a reservoir that immerses the surfaces in a volume of confined fluid. The fluid element can include nozzles that direct flow of maturation fluid towards the biopolymer tissue and the second surface.

According to another aspect of the invention, the second support element is adapted for receiving and mounting a second biopolymer tissue such that the second support surface contacts the second biopolymer tissue.

According to another feature of the invention, the second surface of the second support element is spaced from the tissue along a first axis, and the relative motion element translates the tissue in a plane substantially transverse to the first axis. The relative motion element hence linearly reciprocates the first support element relative to the second support element.

The relative motion element typically translates the biopolymer tissue received and mounted by the first surface of the first support element relative to the second surface of the second support element at speeds ranging between about 0.5 cm/sec and about 50 cm/sec.

According to yet a further feature, the invention includes an element for varying the spacing, i.e., the gap, between the first and second tissue surfaces. The gap can typically be varied between about 0 mm (where direct contact occurs) and about 5 mm. In one aspect, the gap can be eliminated such the tissue surface contacts the second support surface and the relative motion element slidingly and frictionally engages the tissue surface and the second surface.

According to yet another aspect, the invention includes a compression element for subjecting at least the tissue to selected compressive pressure. The compression element can be adapted for generating a compressive pressure on tissue of between about 0 psi and about 100 psi. The compression element can compress the biopolymer tissue mounted on the first surface of the first support element against the second support element, thereby subjecting the tissue to a compressive force. The compressive force can be applied in the absence of relative motion between the first tissue surface and the second surface, or with relative motion therebetween, such that the surfaces slidingly engage and frictional forces as well as compressive pressure are exerted on the tissue surface.

The maturation fluid is typically a fluid that resembles the naturally occurring synovial fluid. For example, the maturation fluid can be a dialysate of blood plasma, or an imitation thereof, that contains hydraulic acid. For maturing a replacement cartilage tissue, the tissue is seeded with chondrocyte cells that can be obtained from tissue samples that include cells from bone marrow or differentiated articular cartilage. Typically, cells are dissociated enzymatically with collagenase and cultivated in vitro to expand upon the primary cell populations. For seeding a biopolymer replacement tissue formed of a biopolymer foam typical cell suspensions provide between about $5 \times 10^4$ and about $1 \times 10^6$ cells per milliliter of foam.

Many variations of the present invention are possible. According to one embodiment, an apparatus according to the invention includes a fluid reservoir for holding a maturation fluid, a first support element, such as a block, adapted for mounting a first sheet of biopolymer tissue, and a second support element, such as another block, adapted for mounting a second sheet of biopolymer tissue spaced, typically along a vertical axis, from the first biopolymer tissue to form a substantially uniform gap therebetween. The first and second support elements are positioned relative to the reservoir so as to immerse at least a portion of the first and second biopolymer tissues in the maturation fluid, thereby introducing the maturation fluid to the gap so as to contact the first and second biopolymer tissues.

A translation element can translate the first support element relative to the second support element so as to translate the first tissue relative to the second tissue. The translation element can be an electromechanical actuator, coupled to the first support element, for linearly reciprocating the first support element, typically along an axis transverse to the vertical axis.

According to another aspect, the apparatus further includes a compression element coupled to at least one of the first and second support elements for pressing together the first and second biopolymer tissues. The compression element can include a platform, coupled to one of the support elements, for receiving a weight. The gravitational force on the weight is transferred to one of the support elements for pressing the support elements together.

In yet a further aspect, a variable spacing element, such as translation stage, can be included for varying the spacing between the first and second biopolymer tissues.

In another embodiment, the invention includes a rotatable inner cylinder support element having an outer circumferential surface adapted for mounting a first biopolymer tissue such that the mounted biopolymer tissue has a first outwardly-facing tissue surface. An extended arcuate outer support element, such as a hemi-cylinder, is spaced from the inner cylinder and has an inner mounting surface adapted for mounting a second biopolymer tissue having an inwardly facing tissue surface. The rotatable inner cylinder and the outer hemi-cylinder are spaced apart such that the outwardly facing tissue surface is spaced from the inwardly facing tissue surface to form a gap therebetween, and the rotatable inner cylinder and the outer hemi-cylinder are operatively arranged with a fluid reservoir such that the maturation fluid held therein is introduced to the gap and contacts at least a portion of the inwardly and outwardly facing tissue surfaces. The apparatus further includes a rotating element, such as an electric motor, for rotating the rotatable inner support cylinder. Typically, the rotatable inner cylinder and the hemi cylinder are mounted coaxially.

In one aspect of this embodiment, the gap between the outwardly and inwardly facing tissue surfaces can vary. In another aspect of the invention, the outwardly facing tissue surface is spaced from the inwardly facing tissue surface by between about 0 mm and about 5 mm. The apparatus can further include a compression element for compressing together the inwardly and outwardly facing tissue surfaces. In another aspect, the tissue surfaces can be slidingly engaged, with or without compressive pressure, and the tissue surfaces can be compressed together, with or without relative motion therebetween.

In yet another embodiment, an apparatus according to the invention includes a housing having first and second bores formed therein, the first bore having first and second ends and extending along a first longitudinal axis, and the second bore having first and second ends and extending along a second longitudinal axis disposed at an angle, typically transverse, to the longitudinal axis of the first bore. The second end of the second bore intersects and fluidly communicates with the first bore between the first and second ends of the first bore.

An extended piston is disposed for travel in the first bore, and has an extended piston first face, an extended piston second face, and an interconnecting section extending between the first and second faces. Adjacent the first and second piston faces are longitudinally extending first and second piston skirts, respectively, that are separated by a selected gap from the wall of the first bore. An outer surface of the interconnecting section is adapted for receiving and mounting a first biopolymer tissue. A transverse piston is disposed for travel in the second bore, and has a transverse piston first face and a transverse piston second face, the second face being disposed for receiving and mounting a second biopolymer tissue facing the first biopolymer tissue. Typically, the transverse piston includes first and second transverse piston skirts that are adjacent the first and second transverse piston faces, respectively, and are separated by a selected gap from the wall of the second bore.

The extended piston divides the first bore into a first volume, bounded in part by the extended piston first face and the first end of the first bore, and a second volume, bounded in part by the extended piston second piston face and the second end of the first bore. The first and second bores intersect and define a third volume bounded in part by the outer surface of the interconnecting section of the extended piston and the transverse piston second face. A fourth volume is bounded in part by the first end of the second bore and the first face of the transverse piston.

Fluid ports in the bores can allow the transfer of a first fluid, such as maturation fluid, from a fluid supply element, or system, to selected volumes, such as to the first, second and fourth volumes. A fluid port can be included for direct transfer of fluid to the third volume. Alternatively, fluid can be transferred to and from the third volume from the first, second or fourth volumes in various manners, such as an orifice in one of the piston faces, or a suitable gap between the skirt of a piston face and the wall of the housing.

A fluid supply system can selectively transfer fluid to and from, and modulate the pressure of fluid in, the above volumes for providing relative motion between the tissues, for varying the gap between the tissues, for exerting a compressive force on the tissues, and for slidingly engaging the tissues with or without a compressive force. The fluid supply apparatus can include a fluid reservoir, a fluid pump, a pressure regulator, and appropriate valves and conduit for controlling fluid flow to the various fluid ports of the above embodiment. For example, selectively transferring fluid to and from the first and second volumes can selectively translate the extended piston in the first bore.

According to yet another embodiment, apparatus according to the invention resembles a "rolling pin," and has an inner cylinder having a first radius of curvature disposed within the lumen of an outer cylinder. The inner and outer cylinders extend along parallel first and second central axes, respectively. The first central axis can be offset, along a line transverse to the central axes, from the second axis.

The inner cylinder has an outer surface for receiving a first biopolymer tissue having an outwardly facing tissue surface. The outer cylinder includes a wall, having an inner face, bounding the lumen, and for receiving a second biopolymer tissue having an inwardly facing tissue surface. The outwardly facing tissue surface of the first biopolymer tissue mounted on the inner cylinder faces the inwardly facing tissue surface of the second biopolymer tissue mounted on the outer cylinder.

In one aspect of the invention, the inwardly facing tissue surface is spaced from the outwardly facing tissue surface by a gap. The apparatus can include, as in other embodiments, a spacing element for varying the gap, such as an element for moving the inner cylinder relative to the outer cylinder in a direction transverse to the central axes. For example, the inner cylinder can be mounted on a shaft, and the position of the shaft can be varied for varying the gap between the tissue surfaces. The gap between the tissue surfaces can be non-uniform, i.e., the gap can vary around the circumference of the cylinders. For example, the spacing element can move the inner cylinder shaft such that the inner cylinder central axis is offset from the outer surface central axis.

According to another feature, the invention includes an element for introducing a maturation fluid into the gap for contacting the outwardly and inwardly facing tissue surfaces. For example, the inner and outer cylinders can be arranged with a fluid reservoir such that the maturation fluid enters and at least partially fills the lumen of the outer cylinder.

According to one aspect, the invention includes an element for rotating the inner cylinder and/or the outer cylinder. For example, the element can be a motor coupled to the shaft of the inner cylinder. The motor can be operative with the spacing element such that the gap can varied. For example the motor and shaft can be supported by a fixture that is moved by the spacing element.

According to another feature, the outwardly facing tissue engages, i.e., contacts, the inwardly facing tissue along a engagement line substantially parallel with the central axes. For example, the spacing element can adjust the offset of the cylinder central axes such that the tissue surfaces engage along the engagement line. In another aspect of the invention, one of the inner or outer cylinders can be coupled to a rotational drive element, such as a motor, for rotating the cylinder. The other cylinder can be fixed, such that the tissues slidingly engage at the engagement line, or the other cylinder can be rotationally mounted, such as with bearings or other rotational support element, so that the cylinder being rotated by the rotational drive element rotates the other cylinder. The outwardly facing and inwardly facing tissues thus frictionally engage at least along the engagement line, but do not frictionally and slidingly engage.

According to yet another feature of the invention, a compression element presses the outwardly facing tissue and the inwardly facing tissue together to exert selected compressive force on the outwardly and inwardly facing tissue surfaces, typically along the engagement line.

In a further feature of the invention, an element is included for translating the inner cylinder and outer cylinders relative to each other to vary the offset between the central axes thereof such that the line of engagement is circumferentially varied about the inwardly facing tissue surface. For example, the inner cylinder can be mounted on a shaft that is coaxial with the central axis of the inner cylinder. The shaft can be rotationally mounted by a bearings on each end of the shaft to a mounting fixture. The mounting fixture can be translated in an arcuate, typically circular, path in a plane transverse to the central axes of the inner and outer cylinders, such that the line of engagement varies circumferentially about the inwardly facing tissue. The inner cylinder can rotate, due to the contact along the line of engagement between the inwardly facing and outwardly facing tissues, as the inner cylinder is translated within the lumen of the outer cylinder. The outwardly and inwardly facing tissue surfaces thus frictionally engage, but do not frictionally and slidingly engage.

Translation of the cylinders relative to each other may be combined with at least one rotational drive element, such as a motor, for rotationally driving at least one of the cylinders.

The above embodiments involve attaching a biopolymer tissue to a portion of the apparatus, such as a support element, which can include a block, a portion of a piston, or a surface of a cylinder. A biopolymer tissue can be a foam, and can be attached by a variety of means, such as bone cement, to a support element, or can be cast as a foam directly on a support element. Casting of foams is discussed below. It is believed that attaching a tissue with bone cement may have certain advantages. The maturation process may promote intergrowth of the biopolymer tissue and the bone cement, and a portion of the bone cement can be implanted in the body with the biopolymer tissue. The bone cement attached to the tissue can be cemented to bone existing in the body.

Forces need not be applied to the replacement tissue throughout the maturation process, nor need the composition of the maturation fluid remain constant. For example, for expansion of the seed cell population, the maturation fluid can contain cell nutrients. During expansion of the chondrocyte seed population, forces are typically not applied to the replacement tissue. However, to provide biosignals to promote cell differentiation and/or secretion of the extracellular matrix material, forces are typically applied and cell nutrients are of lesser importance as a component of the maturation fluid, than for example, growth factors for promoting proper cell differentiation. Thus the apparatus and methods of the present invention are intended to provide a versatile tissue-maturation tool that one of ordinary skill in the art, based on the disclosures herein, can use to tailor the conditioning of a replacement tissue. According to the invention, tissue can be matured not only for implantation but as part of a research study, in which case the exact program of forces and maturation fluid composition could be varied to determined the effect on tissue development. Research efforts may result in a improved or optimized program that is then applied to the maturation of tissue constructs for use in vivo.

The invention also includes methods practiced in accordance with the teachings of the invention presented herein.

BRIEF DESCRIPTION OF THE DRAWINGS

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

FIGS. 2A through 2C illustrate cross-sectional views of another embodiment of an apparatus according to the invention for maturing biopolymer replacement tissue prior to implantation of the tissue into a body. FIG. 2B is an exploded view of the vessel employed in FIG. 2A. FIG. 2C is a cross-sectional view, taken along section line C—C in FIG. 2A, of the apparatus illustrated in FIG. 2A.

FIG. 4B is a cross-sectional view taken along section line B—B of FIG. 4A illustrating a motor for powering the apparatus shown in FIGS. 4A and 4B.

FIG. 8 is a partial cross-sectional view of an alternate embodiment of the spherical applicator of FIG. 7 according to the teachings of the present invention.

DESCRIPTION OF THE ILLUSTRATED EMBODIMENTS

Figure 1:
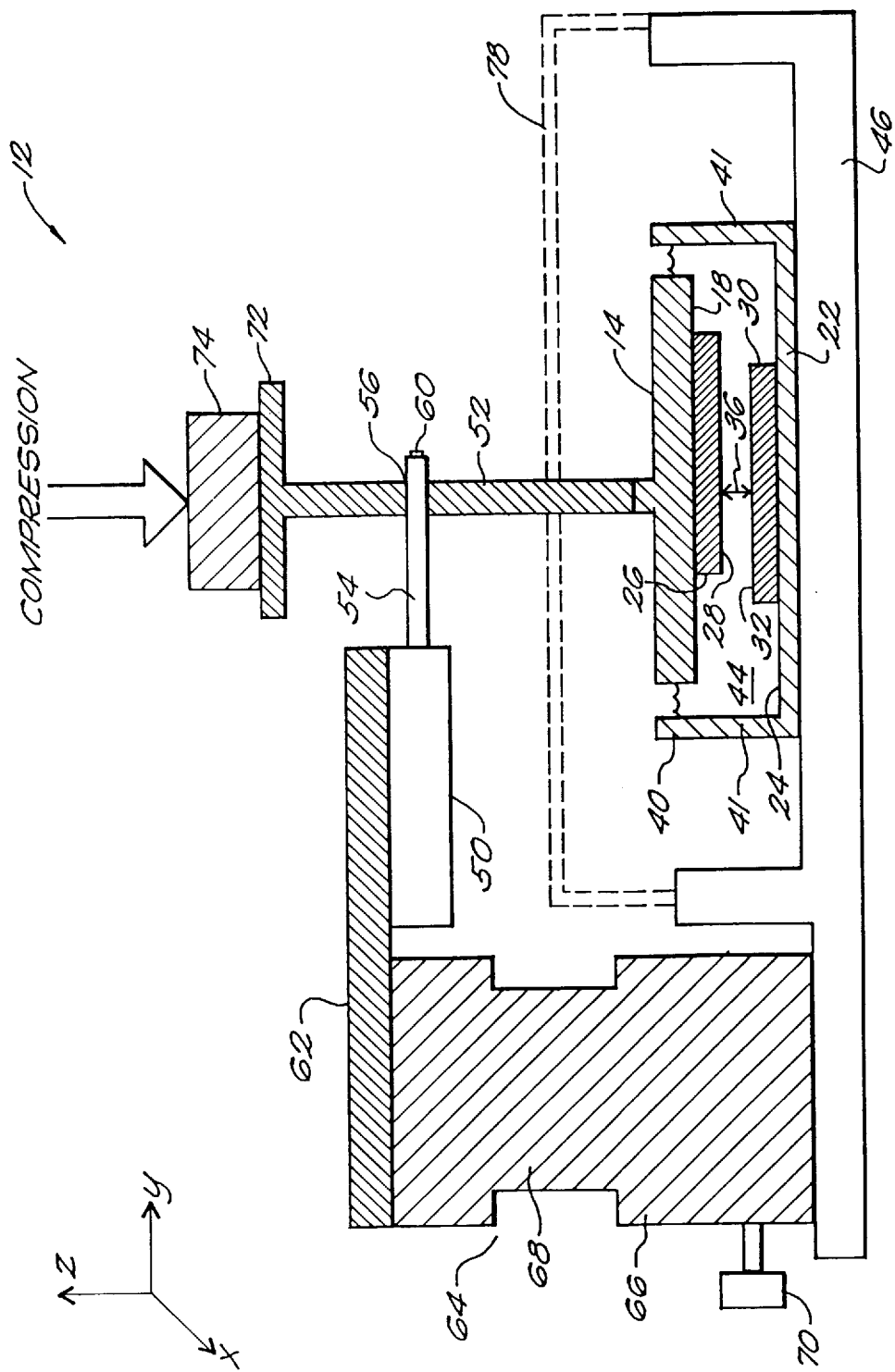
FIG. 1 is a cross-sectional view of one embodiment of an apparatus for maturing biopolymer replacement tissue prior to implantation of the tissue into the body according to the teachings of the present invention.

FIG. 1 shows an apparatus 12 for maturing biopolymer replacement cartilage tissue prior to implantation of the cartilage tissue in, for example, a knee joint. The illustrated tissue maturation apparatus 12 includes a first support element 14 having a first outer surface 18 and is adapted for receiving and mounting biopolymer tissue 26. A second support element 22 having an outer surface 24 is spaced along the Z axis, as shown in FIG. 1, from the first support element 14. The first outer surface 18 mounts a first sheet of biopolymer tissue 26. A layer of bone cement (not shown) can be interposed between the first sheet of tissue 26 and the outer surface 18 to attach the sheet of tissue 26 to the surface 18. A contact surface 28 of the biopolymer tissue 26 is spaced by a substantially uniform gap 36 from a second outer surface 32 of a second sheet of biopolymer tissue 30 mounted to the second support element 22. The second sheet of biopolymer tissue 32 is optional, and if not present, the gap 36 separates the contact surface 28 of the first biopolymer tissue 26 from the outer surface 24 of the second support element 22.

A reservoir 40 confines a maturation fluid 44 therein such that the maturation fluid 14 substantially fills the gap 36 and is in communication with at least a portion of each of the biopolymer tissue surfaces 28 and 32. The second support element 22 and sides 41 form the reservoir 40. The apparatus base 46 supports the reservoir 40 as well as other components of the tissue maturation apparatus 12, as described below.

A vertical rod 52 and a horizontal actuating rod 54 couple the first support element 14 to a relative motion element 50. The horizontal actuating rod 54 can have a bore 56 formed therethrough, through which the vertical rod 52 passes. Vertical rod 52 can be affixed to the actuating rod 54 via a set screw 60 disposed axially in the actuating rod 54. The relative motion element 50 can be a linear actuator motor which reciprocates the actuating rod 54, and hence the first support element 14 and the first cartilage tissue 26 attached thereto, along the Y axis.

The maturation fluid 44 in the gap 36, in response to the linear reciprocating motion of the first cartilage tissue 26, generates a shear force that acts on the first surface 28 of the first tissue sheet 26, and, if the second tissue sheet 30 is present, on the second tissue surface 32. The magnitude of the shear force generated by the apparatus 12 is a function of the nature of the maturation fluid, the size of the gap 36, and the stroke and frequency of the linear reciprocating motion of the first tissue imposed by the linear actuator 50.

The support plate 62 supports the linear actuator 50 and couples the actuator 50 to a variable spacing element 64. The variable spacing element 64 includes a lower fixed portion 66 and an upper translation stage 68. Rotation of knob 70 translates the upper stage 68 relative to the fixed portion 66 along the vertical or Z axis, thereby varying the gap 36 between first biopolymer tissue surface 28 and the second biopolymer tissue surface 32, or if the second biopolymer tissue 30 is omitted, between the first biopolymer tissue surface 28 and the surface 24.

The upper end of the vertical rod 52 includes a platform 72 adapted for receiving a weight 74. Loosening the set screw 60 allows the vertical rod 52 to move downwards until the first surface 28 of the first biopolymer tissue 26 contacts the second surface 32 of the second biopolymer tissue 30. Various weights can be placed on the platform 72 for generating a selected pressure between the surfaces 28 and 32 of the biopolymer tissues 26 and 30. The actuating means 50 can provide a relative motion as the pressure due to weight 74 is applied to the biopolymer tissue surfaces 28 and 32. Optionally a cover 78 can be employed to cover the reservoir 40, first mounting element 14 and second mounting element 22, as well as biopolymer tissues 26 and 32 and the maturation fluid 44.

The cartilage articulation apparatus 12 is an open system, i.e., exposed to the surrounding environment, and is typically disposed in an incubator (not shown) that maintains a 10% $CO_2$ atmosphere. The 10% $CO_2$ atmosphere of the incubator communicates with the maturation fluid or culture medium in the reservoir 44 to maintain the pH of the maturation fluid 44 in a selected range. A suitable linear actuator 50, having a stroke of 1 inch, is available from Menzinuer Aircraft Components, Inc. of Vista, Calif. as part number MAC-S4-102. The MAC-S4-102 operates on low voltage direct current, and the polarity of the voltage can be periodically reversed so as to reciprocate at approximately 2 strokes per minute, via switching gear known to those of ordinary skill in the art. The support element 14 and the second support element 42 can be fabricated from polymeric or TEFLON blocks or other suitable biocompatible, non-leaching material. The cartilage tissues 26 and 30 can be affixed thereto with calcium phosphate bone cement. A suitable vertical translation stage 64 is available as part number D39928 from the Edmund Scientific Company of Barrington, N.J.

Figure 2C:
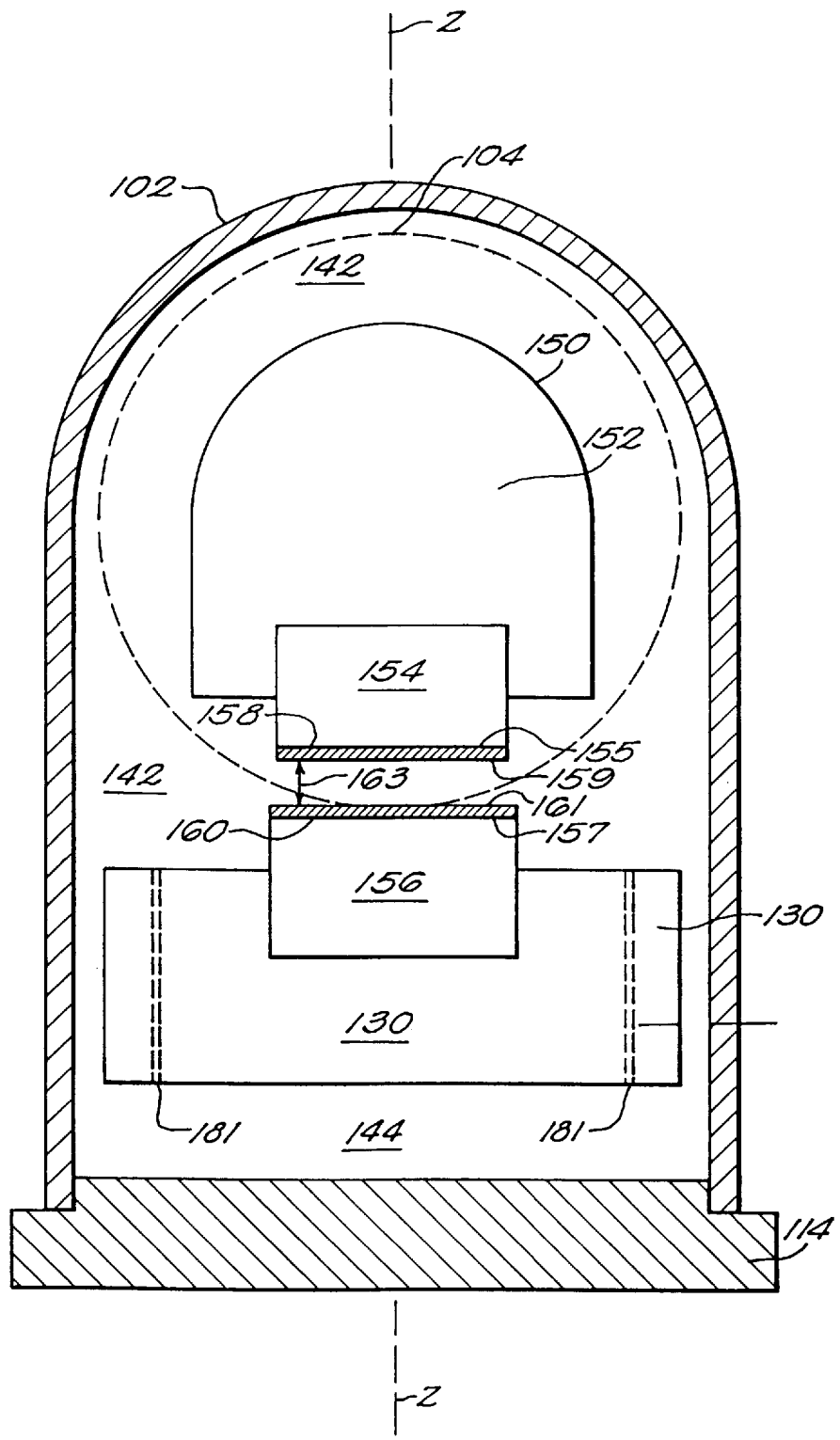

FIGS. 2A, 2B, and 2C illustrate an alternate embodiment of a tissue maturation apparatus 100 according to the present invention. FIG. 2B is an enlargement of a portion of FIG. 2A, and FIG. 2C is a sectional view of apparatus 100 taken along section line C—C.

The tissue maturation apparatus 100 shown in FIGS. 2A through 2C is a closed system, i.e., it is not in communication with the ambient atmosphere. The tissue maturation system 100 includes a housing 102 having two bores formed therein. The first bore 104 extends along the axis Y—Y and is intersected by a transverse bore 106 that extends along the axis Z—Z. The first bore is bounded by a first bore end 110 and a second bore end 112, and in part by a first transverse bore end 114. An extended piston 120 is disposed for travel in the first bore 104 and includes a first extended piston face 122 and a second extended piston face 124. A transverse piston 130 is disposed for travel in the transverse bore 106 and has a first transverse piston face 132 and a second transverse piston face 134. The extended piston 120 divides the first bore 104 into a first volume 138 bounded along the Y axis by said first extended piston face 122 and the first bore end 110, and into a bore volume 140 bounded along the Y axis by the second extended piston face 124 and the second bore end 112. Similarly, the transverse piston 130 creates a third volume 142 bounded in part by the second transverse piston face 134 and the outer surface 150 of the interconnecting section 152 of the extended piston 120. The transverse piston 130 also divides the transverse bore into a fourth volume 144 bounded along the Z axis by the first transverse bore end 114 and the first transverse piston face 132.

A portion of the outer surface 150 of the interconnecting section 152 of the extended piston 120 is adapted so as to form a first mounting element 154 to mount a first biopolymer tissue construct. Likewise, the transverse piston face 134 is apertured to form a second mounting element 156 for mounting a second biopolymer tissue construct. Specifically, the first surface 155 of the first mounting element 154 mounts a first sheet of biopolymer tissue 158, typically spaced across a substantially uniform gap 163 from a second sheet of biopolymer tissue 160 mounted by a second face 157 of the second mounting element 156.

Fluid ports 170 and 172, formed in the first end 120 of the housing 102 communicate a maturation fluid 44 (not shown) with the first volume 138. Similarly, fluid ports 174 and 176 in the second end 112 of the housing 102 communicate the maturation fluid 44 with the bore volume 140. Fluid ports 178 and 180 in the first end 114 of the transverse bore 106 allow communication of maturation fluid 44 with transverse bore volume 144. The maturation fluid 44 is selectively supplied or drawn through fluid ports 170, 172, 174 and 176, as required, to reciprocatingly translate the extended piston 120 within the bore 104 along the Y axis. Selectively supplying or drawing the maturation fluid 44 from fluid ports 178 or 180, as required, varies or adjusts the gap 163 and the compressive forces between the biopolymer tissue 158 and the biopolymer tissue 160. Thus, provision of a maturation fluid to fluid ports 170, 172 or 174, 176 allows for reciprocating motion of the piston and hence of the first biopolymer tissue mounted thereto. The reciprocating motion moves the first tissue relative to the second tissue.

The frictional and compressive forces applied to the tissues 154, 156 can be adjusted or varied according to a selected program of compressional loading and unloading by a control system (not shown). The controller can be in open or closed feedback connection with the apparatus to vary or to maintain the frictional and/or compressional forces applied to the tissues. Those of ordinary skill will readily be able to determine in light of the present teachings the type and magnitude of the forces that the tissue is subjected to, based upon the intended site of the tissue, the intended use, the type of maturation fluid and seeded cells, and the type and size of the apparatus.

A sufficient amount of the maturation fluid 44 (not shown) should be present in the gap 163 so as to contact a portion of the first biopolymer tissue surface 159 and a portion of the second biopolymer tissue surface 161 such that relative motion of the tissue surfaces creates shear forces thereon. The maturation fluid 44 can enter the bore volume 142 between the ends 123, 125 by, for example, passing through a gap 182 formed about the outer diameter of the piston and between the extended piston and the walls of the housing 102, as illustrated in FIG. 2C. The maturation fluid then flows between bore volumes 138, 140, and 142, such that it can contact the surfaces 159 and 161 of tissues 158 and 160, respectfully. The gap 182 is not so large as to prevent a reasonable pressure differential to form easily and consistently between the bore volumes 140 and 138 to translate the extended piston 120 in the bore 104 to provide relative, reciprocating motion between the biopolymer tissue surfaces 159 and 161. Such a gap 182 is not the only means by which the maturation fluid 44 can be supplied to the gap 163 so as to contact the biopolymer tissue surfaces 159 and 161. For example, an orifice 181, FIG. 2C, of a selected diameter may be provided through transverse piston 130, or an appropriate gap (not shown) provided between the skirt of piston 130 and the walls of housing 102, to provide a flow of maturation fluid 144 from the bore volume 144 to the bore volume 142. Such an orifice can be used in conjunction with gap 182 to allow maturation fluid to flow from the bore volume 144 to the volume 142, and then to the bore volumes 138 and 140. Alternatively, a fluid port (not shown) can be added to the housing 102 to communicate maturation fluid directly with bore volume 142.

Figure 3:
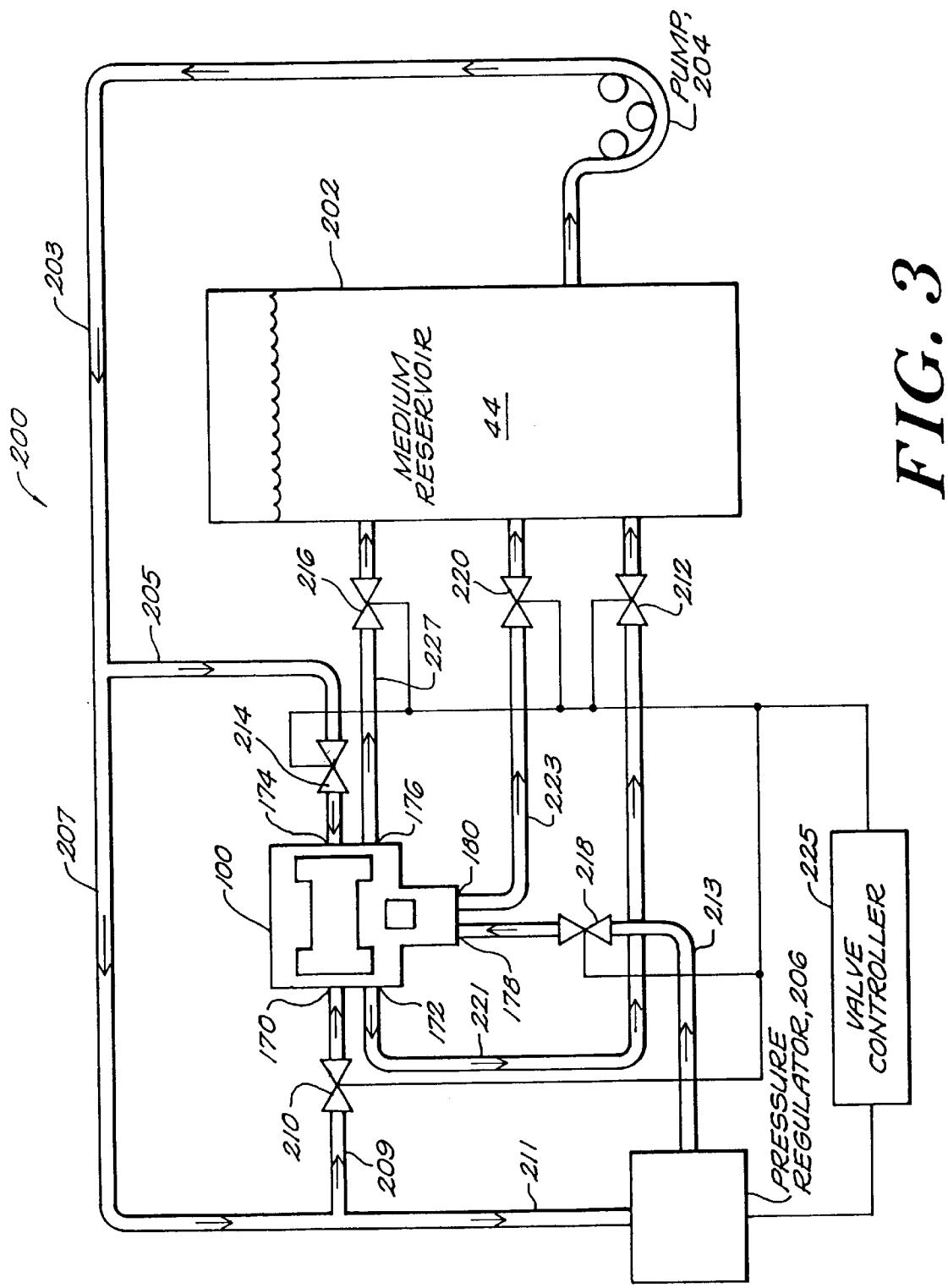
FIG. 3 is a schematic system flow diagram of a maturation fluid supply system for supplying fluid to, and for actuating, the tissue maturation apparatus of FIGS. 2A through 2C.

FIG. 3 illustrates a fluid supply system 200 for supplying maturation fluid to the tissue maturation chamber 100. The illustrated system 200 provides a selected flow of maturation fluid to selected bore volumes for reciprocatingly translating the extended piston 120 in the bore 104 and for translating the transverse piston 130 in the transverse bore 106 to adjust the gap 163. In addition, the system 200, in conjunction with the tissue maturation chamber 100, provides a flow of maturation fluid to the gap 163 so as to immerse at least a portion of the tissue surfaces 159 and 161 in maturation fluid. The fluid supply system 200 can also provide a selected pressure of maturation fluid in the volume 144, and hence to piston 130 for applying selected pressure between tissue surfaces 159 and 161.

The fluid supply system 200 depicted in FIG. 3 includes a maturation fluid reservoir 202 containing maturation fluid 44, a pump 204, a pressure regulator 206, a valve controller 225 and valves 210, 212, 214, 216, 218 and 220, all connected as shown. In particular, the reservoir 202 is connected by fluid conduits 203, 205, 207 and 209 to the maturation chamber 100 through valves 210 and 214. The valves 210 and 214 selectively control the introduction of fluid to the maturation chamber, as indicated by the flow arrows. Fluid conduit 211 connects the conduit 207 to the pressure regulator 206. The pressure regulator output is connected by fluid conduit 213 to the maturation chamber 100 through valve 218. The maturation chamber dispels maturation fluid through selected output conduits, for example, through output fluid conduits 221, 223 and 227, which connect at the other end to the reservoir 202 through valves 212, 220, and 216, respectively.

The illustrated valve controller 225 is in feedback circuit with the pressure regulator 206 and valves 210, 212, 214 and 216 to modulate selectively the flow of the maturation fluid 44 to fluid ports 170, 172, 174 and 176, respectively, for reciprocatingly translating the extended piston 120 in the bore 104. For example, opening valve 210 and closing valve 212 allows the maturation fluid 44 to flow, via port 170, into volume 138 and to increase the pressure of the maturation fluid 44 therein. This displaces the extended piston 120 to the right in FIG. 2A. Closing valve 214 and opening valve 216 allows the maturation fluid 44 to flow through fluid port 176 from the bore volume 140, thus releasing maturation fluid pressure therein. Hence the extended piston 120 translates to the right in FIG. 2A. One of ordinary skill in the art, based on the disclosures herein, will readily appreciate how selective control of the valves shown in FIG. 3 reciprocatingly translate the piston 120, translate the transverse piston 156 for selecting a pre-determined gap size 163, and apply a selected pressure to the transverse piston 130 for providing a selected pressure on tissue surfaces 159 and 161.

Similarly, operating the valves 218 and 216 allows the spacing between the tissues 158 and 160 to be varied or pressure to be applied between the tissues 158 and 160. For example, opening the valve 218 to admit a selected amount of fluid and then closing both valves 218 and 220 maintains a selected volume of fluid in the bore volume 144 such that a selected gap 163 may be maintained between the tissues 160 and 158. If necessary, the valve 218 can remain open and the pressure regulator 206 can maintain a nominal pressure volume to compensate for fluid leakage therefrom to bore volume 142. To apply a selected compressive force, i.e., pressure between the tissues 158 and 160, valve 218 can be opened and the pressure regulator 206 operates to adjust the fluid pressure to maintain an elevated fluid pressure within volume 144, thereby forming a selected pressure between tissues 158 and 160.

Figure 4A:
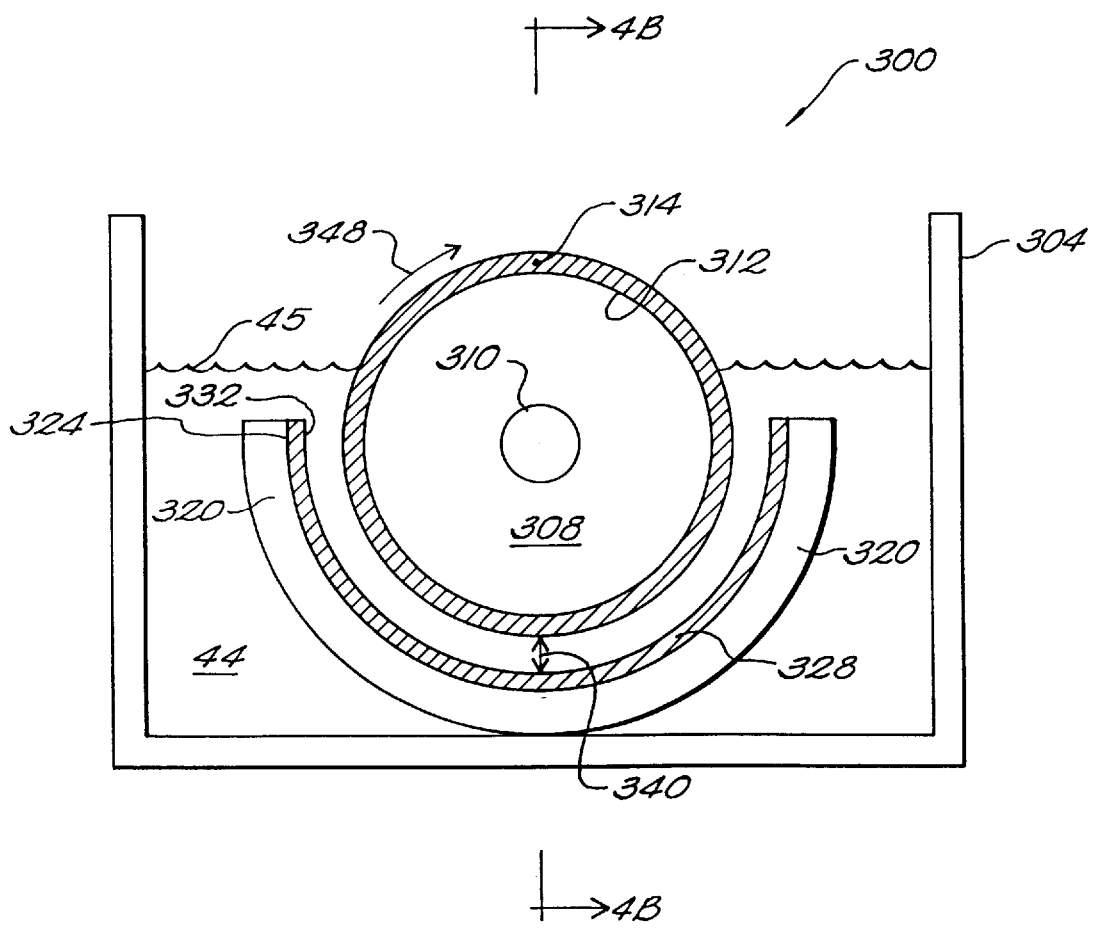
FIGS. 4A through 4B are cross-sectional views of still another embodiment of an apparatus for maturing replacement tissue prior to implantation of the tissue into a body.
Figure 4B:
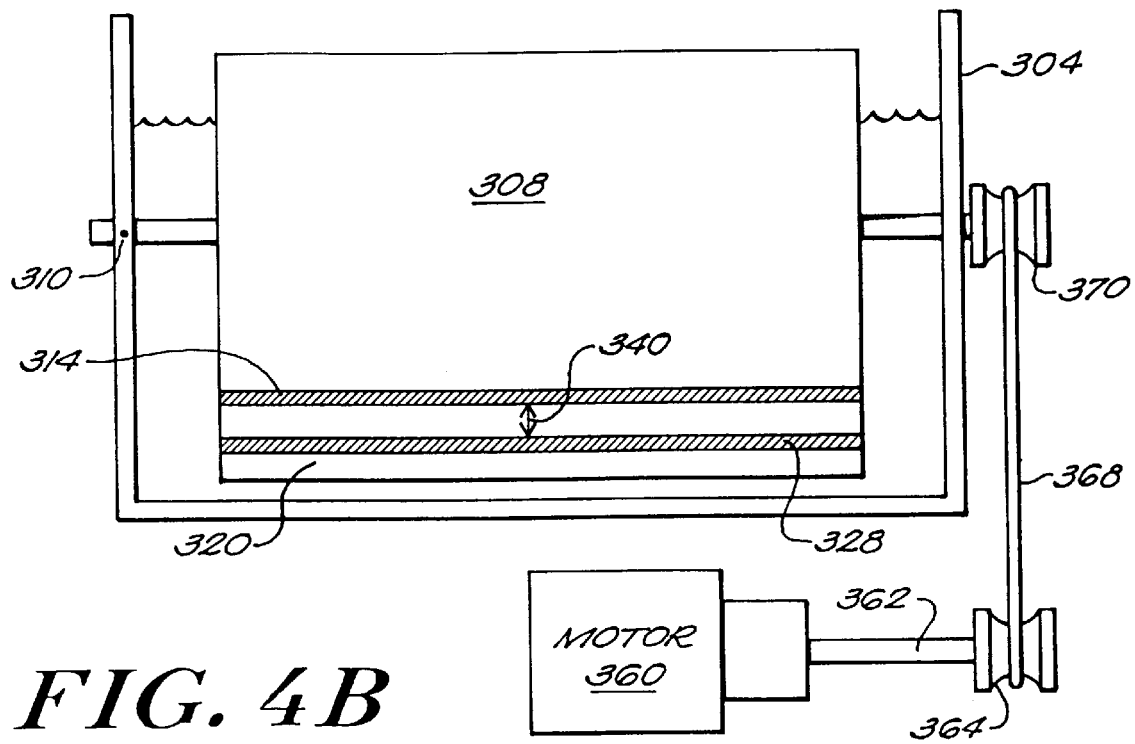

FIGS. 4A and 4B show another embodiment 300 of an apparatus for maturing biopolymer replacement tissue. An inner cylinder 308 mounts on an outer surface 312 thereof a first biopolymer tissue 314 having an outwardly facing tissue surface 316. A stationary outer arcuate and extended support element such as the hemi-cylinder 320 mounts on an inner surface 324 thereof a second biopolymer tissue 328. The tissue 328 includes an inwardly facing tissue surface 332. A shaft 310 mounts the cylinder 308 such that there is a selected gap 340 between the tissue surfaces 316 and 332. A reservoir 304 confines a maturation fluid, the upper level of which is indicated by the wavy line 45, such that the maturation fluid 44 fills the gap 340 and communicates with tissue 314 and 328, and with tissue surfaces 316 and 332.

FIG. 4B shows a motor 360 having a rotatable shaft 362 and a pulley 364. The pulley is coupled by means of a belt 368 to a pulley 370 mounted on the shaft 310. The shaft 310 is rotatably coupled, such as by bearings and fluid seals (not shown) to the reservoir 304. The motor 360 rotates the cylinder 308, as indicated by arrow 348 in FIG. 4A, for providing relative motion of the cylinder 308 and the transmission of shear forces between tissue surfaces 316 and 332.

Typically, the motor 360 rotates the cylinder 308 such that the first biopolymer tissue surface 316 is translated at speeds ranging from about 0.5 cm per second to about 50 cm per second.

One of ordinary skill in the art, based on the teachings herein, can readily employ further additional appropriate elements for varying the gap 340 and for applying a compressive or frictional force on the tissue surfaces 332 and 316.

Figure 5:
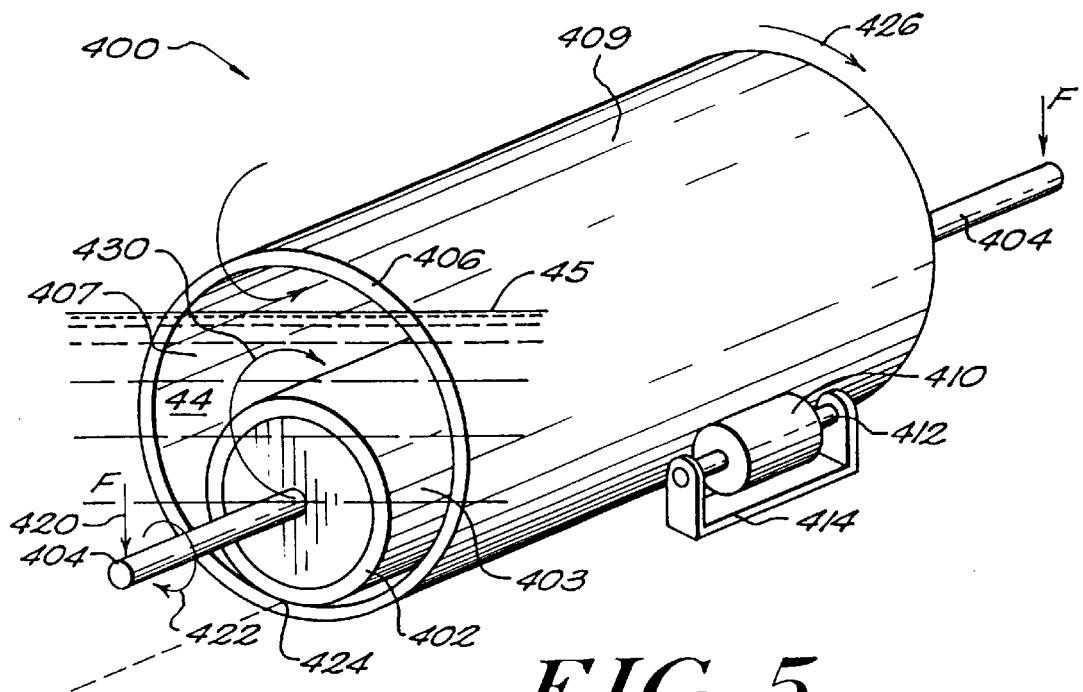
FIG. 5 is a perspective view of yet another embodiment of an apparatus according to the invention for maturing tissue prior to insertion of the tissue in a body.

FIG. 5 schematically illustrates the principle features of another embodiment of a tissue maturation apparatus 400 in accordance with the teachings of the present invention. To facilitate the discussion of certain illustrated features, miscellaneous parts of the apparatus are omitted for clarity, but which have been previously described herein. The illustrated apparatus 400 is similar to that shown in FIGS. 4A and 4B except that the hemi-cylinder 320 is replaced by a full cylinder 406. The inner cylinder 402 can have a radius of curvature significantly different than that of the outer cylinder 406. As shown in FIG. 5, the shaft 404 mounts an inner cylinder 402, which in turn mounts on its outer surface a first biopolymer replacement tissue having an outwardly facing tissue surface 403. An outer cylinder 406 mounts on its inner surface a second biopolymer tissue having an inwardly facing tissue surface 407. The inner cylinder 402 is disposed within a central lumen of the cylinder 406 such that the outwardly facing tissue surface 403 faces the inwardly facing tissue surface 407. Rollers, such as the roller 410 mounted on a shaft 412 and rotatably coupled to a roller mount 414, rotatably support the outer cylinder 406 by contacting the outer surface 409 of the outer cylinder 406. The outer cylinder can thus rotate as indicated by arrow 426. The shaft 404 can be rotatably mounted by a bearing fixed to a frame and can be driven by a motor similar to the arrangement depicted in FIG. 4B.

The outwardly facing tissue surface 403 contacts the inwardly facing tissue surface 407 along the engagement line 424. Rotation of the shaft 404 in the direction indicated by reference numeral 422 causes the outer cylinder 406 to rotate in the direction indicated by arrow 426 due to frictional contact between the two tissue surfaces 403 and 407 along the engagement line 424. A fluid reservoir can confine a maturation fluid such that it contacts the tissue surfaces 403 and 407 at least at the line of engagement 424 therebetween. The inwardly facing tissue surface 407 and the outwardly facing tissue surface 403 frictionally engage along the engagement line 424 but do not slidingly engage. Application of a force 420 downward on shaft 404 subjects the tissue surfaces 407 and 403 to a compressive force.

A second motor can be added to the drive shaft 412 such that the outer cylinder 406 can be rotated independently of the inner cylinder 402. Thus the inwardly facing tissue surface 407 and outwardly facing tissue surface 403 can slidingly engage along line 424. One of ordinary skill in the art will recognize that means can be included with the apparatus 400 shown in FIG. 5 for raising or lowering shaft 404 for maintaining a selected gap between the tissues surfaces 407 and 403 along the engagement line 424. The apparatus 400 disclosed in FIG. 5 does not maintain a substantially uniform gap between the tissue surfaces 403 and 407.

The use of the term "gap" above in connection with the illustrated embodiment indicates that the tissue surfaces do not contact. If a gap exists between the tissue surfaces 407 and 403, the phrase "line of engagement" is intended to designate a line of minimum spacing between the inwardly and outwardly facing tissue surfaces, 407 and 403, respectively.

Figure 6:
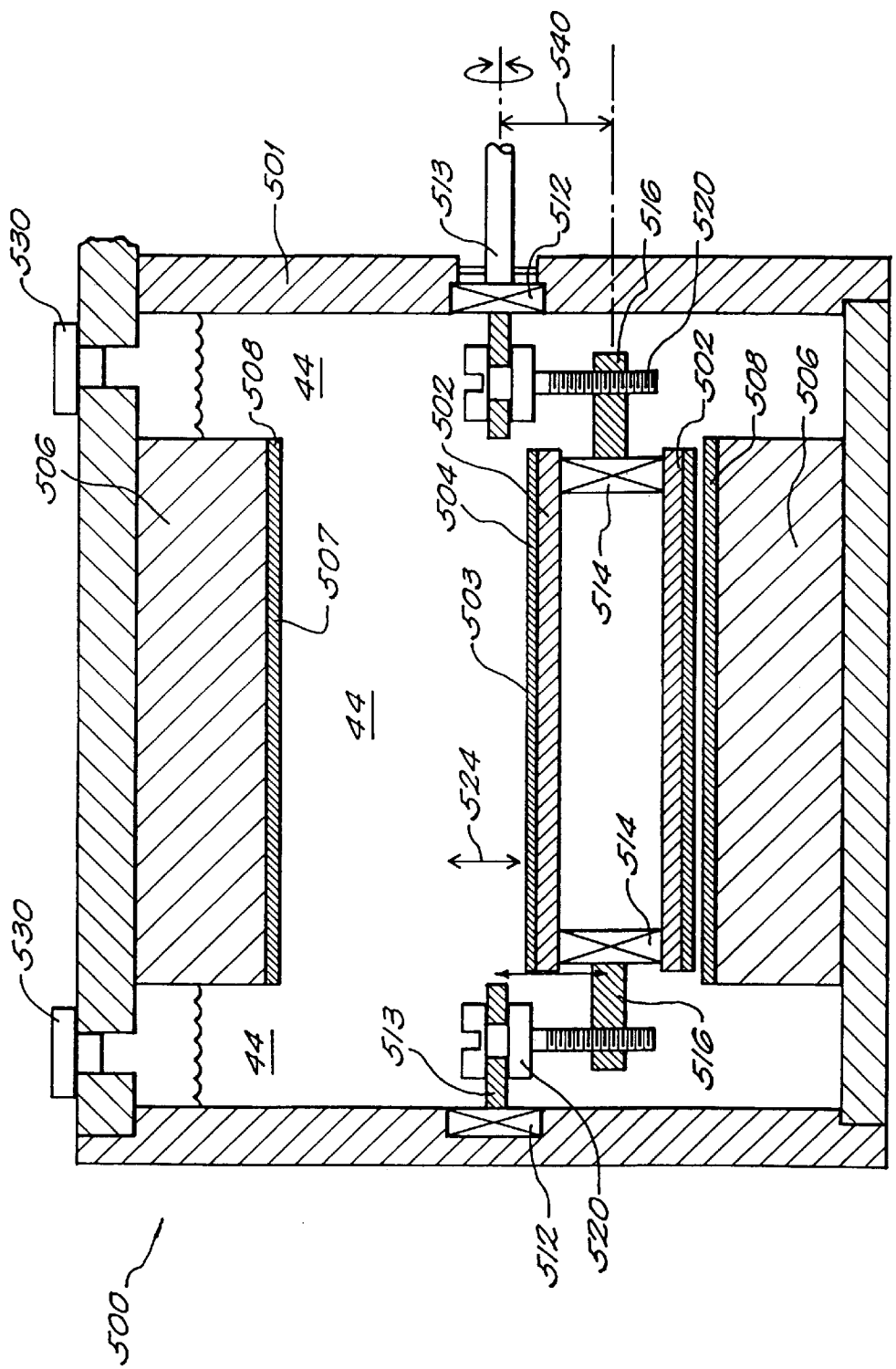
FIG. 6 is a cross-sectional view of one embodiment of an apparatus for maturing tissue in accordance with the features illustrated in FIG. 5.

FIG. 6 illustrates an apparatus for translating the shaft 404 in FIG. 5 along path 430 such that the line of engagement 424 between the inwardly facing tissue surface 407 and the outwardly facing tissue surface 403 is circumferentially varied about the inwardly facing tissue surface 407. The illustrated tissue maturation apparatus 500 includes a housing 501 for confining the maturation fluid 44. The drive shaft 513, offset screws 520, and offset shafts 516 mount an inner cylinder 502 within an outer cylinder 506. The outer surface of the inner cylinder 502 receiving a first biopolymer tissue 504 having an outwardly facing tissue surface 503. The inner surface of cylinder 506 receiving a second biopolymer tissue 508 having an inwardly facing tissue surface 507 facing the tissue surface 503. Bearings 512 rotatably mount the drive shaft 513 to the housing 501. The drive shaft 513 can be driven by a motor and pulley arrangement such as the motor and pulley arrangement disclosed in FIGS. 4A and 4B.

The bearings 514 mount the inner cylinder 502 to offset shafts 516. Offset screws 520 are rotatably mounted and captured by the drive shafts 513 and threadingly engage the offset shafts 516 such that the offset 540 distance between the offset shafts 516 and the drive shafts 513 may be varied by rotating the screws 520. Thus the path 430 in FIG. 5 followed by the offset shafts 516 can be varied such that the outwardly facing tissue surface 503 is spaced by a selected gap from the inwardly facing tissue surface 507. Alternatively, the offset distance between the drive shaft 513 and offset shafts 516 may be selected such that the line of engagement 424 between the inwardly facing tissue surface 403 and the outwardly facing tissue surface 407 is circumferentially varied about the inwardly facing tissue surface 407. Circumferentially refers to a circular path, in a plane transverse to the central axes, around the inwardly facing tissue surface 407. The inner cylinder 502 thus rotates about the bearings 514 due to frictional contact along the line of engagement 424 between the tissue surfaces 403 and 407. The offset screws 520 can be adjusted such that a selected pressure exists on each of the tissue surfaces 503 and 507.

The housing 501 includes media access plugs 530 for filling the interior of the housing with maturation fluid 44 and for adjusting the offset screws 520 for varying the offset distance 510 between the offset shafts 516 and the drive shafts 513. Should the distance indicated by reference numeral 540 be selected such that the tissue surface 503 does not contact the tissue surface 507, means can be added to the apparatus 500 shown in FIG. 6 to independently rotate the inner cylinder 502 as the drive shaft 513 is rotated. Rotating the inner cylinder 502 thus insures that the portion of the tissue surface 503 that is closest to the tissue surface 507 is continuously varied.

Although the embodiments disclosed above typically mount two biopolymer tissues having each having a tissue surface facing, across a gap, a tissue surface of the other tissue, two separate tissues are not considered necessary to condition tissue. A single biopolymer tissue can be conditioned by mounting it so as to face a non-tissue surface across an appropriate gap.

Sheets or other shapes of biopolymer tissue for maturation in accordance with apparatus and methods of the present invention can be received and mounted on mounting elements, or other appropriate mounting surfaces, with bone cement, as indicated above. However, biopolymer tissues for maturation can be cast as a biopolymer foam directly on mounting surfaces, and further processed, if desired, before maturation of the tissue in a maturation apparatus. Accordingly, the deposition and processing of biopolymer foams is discussed below.

Figure 7:
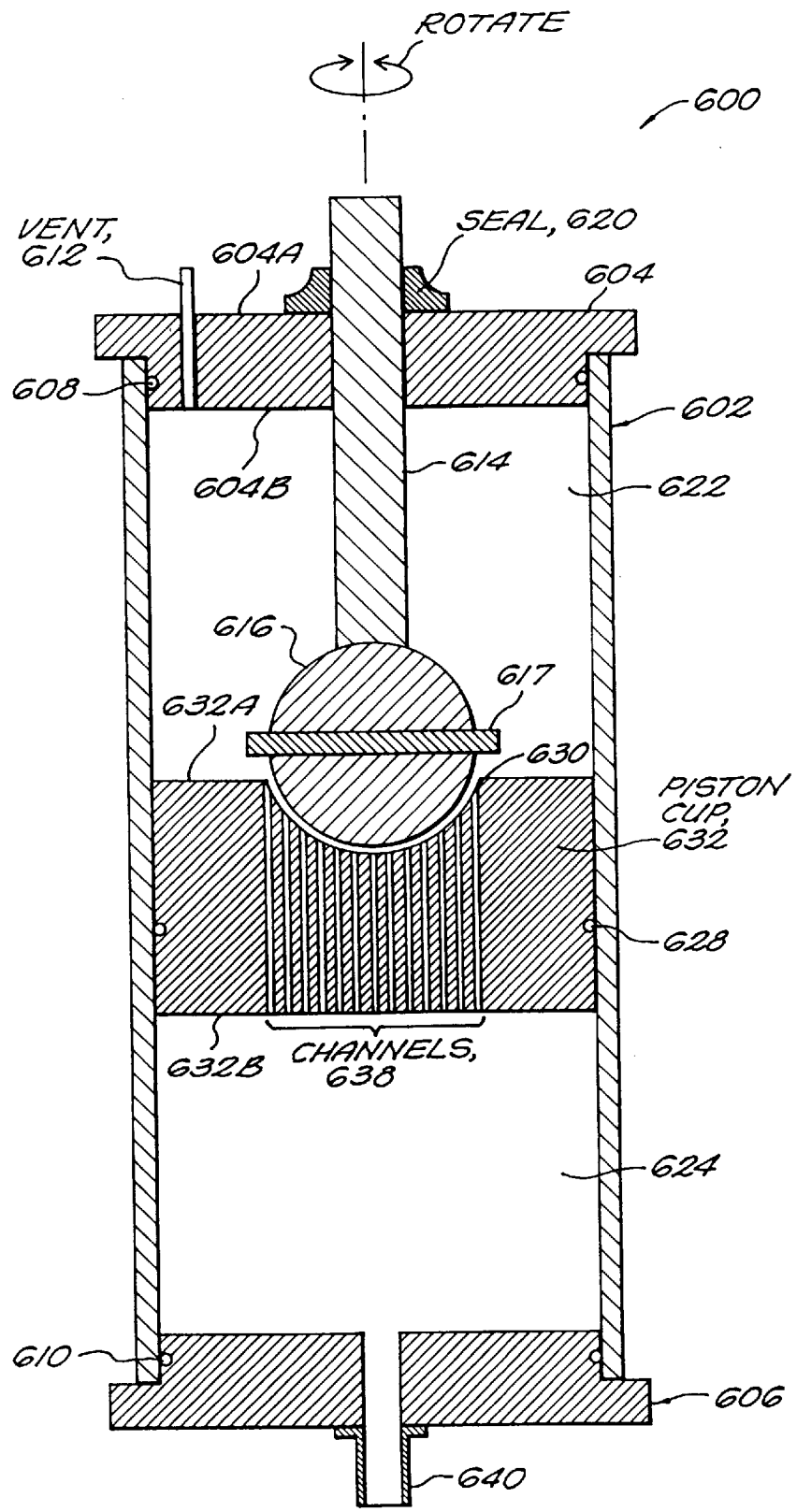
FIG. 7 is a plan view of a double-curvature embodiment of the tissue maturation apparatus according to the teachings of the present invention.

FIG. 7 illustrates another embodiment of a tissue maturation apparatus 600 according to the teachings of the present invention. The illustrated apparatus 600 includes a housing 602 that mounts a pair of endcaps 604 and 606. The endcap 604 mounts an O-ring 608 in an annular channel to form a fluid-tight seal between an inner wall of the housing 602 and the endcap. Likewise, the endcap 606 mounts an O-ring 610 in an annular channel to form a fluid-tight seal between an inner wall of the housing 602 and the endcap. The endcap 604 is apertured with a vent through passage 612 that extends between top 604A and bottom 604B surfaces of the endcap. The vent passage vents air from the housing chamber to enable a fluid to flow therein. The endcap 604 further includes a central aperture that mounts a shaft that terminates at one end with a spherical pressure applicator 616. The spherical pressure applicator 616 can further include a foam clamp 617 disposed about the applicator. A seal 620 mounts to the top 604A of the endcap to prevent fluid leakage from an inner chamber of the housing to the external environment. The illustrated endcap 606 has a port 640 formed therein sized for introducing a fluid from a fluid source to the chamber 624, or for drawing fluid from the chamber.

A piston cup 632 is mounted within the housing chamber and divides the chamber into an input chamber 622 and an output chamber 624. The piston cup 632 has an outer diameter equal to or slightly smaller than the inner diameter of the housing, and preferably seats an O-ring 628 to prevent fluid passage along the outer diameter of the piston cup. Those of ordinary skill will recognize that the piston cup outer surface can be spaced from the inner wall of the housing to allow passage of fluid therealong.

The illustrated piston cup 632 has a concave surface feature 630 formed on the top surface 632A. The concave surface feature 630 has a radius of curvature that closely matches the radius of curvature of the spherical support 616. The input chamber is fluidly coupled to the output chamber 624 by a plurality of perfusion channels 638 that extend from the concave surface feature 630 to the bottom surface 632B of the piston cup 632. The perfusion channels allow a selected degree of maturation fluid introduced to the input chamber 622 to pass or diffuse therethrough and hence between the chambers 622 and 624. The piston cup can be supported in the illustrated position by known means, including rigid fasteners.

The position of the spherical pressure applicator 616 can be varied to define a gap of selected width between the applicator and the concave surface feature 630. For example, the spherical pressure applicator 616 can be raised or lowered to widen or reduce the gap size. The gap size defines among other things the type of force applied to a tissue sheet supported on the top surface 632A of the piston cup 632. For example, the spherical pressure applicator 616 can be positioned so as to contact the tissue to apply a compressive force to the tissue. The spherical pressure applicator 616 can then be rotated whilst in this position to concomitantly apply a frictional force to the tissue. According to another aspect, the spherical pressure applicator 616 can be spaced from tissue by a selected degree. The maturation fluid can flow across the tissue or the spherical pressure applicator 616 can be rotated to create a shear force on the tissue. The curvature of the applicator and the piston cup define a double curvature tissue maturation arrangement that is suitable for conditioning the tissue in the presence of a maturation fluid to particular stresses. The tissue conditioned in this manner is suitable for use as replacement knee cartilage, since the double curvature arrangement mimics the articulation stresses experienced by the joint in its natural environment.

In operation, maturation fluid is introduced to the input chamber 622 and the spherical pressure applicator 616 is positioned to apply a selected shear or compressive force. The spherical pressure applicator 616 can be rotated if desired to further apply a frictional force to the surface of the tissue. During the stressing of the tissue, the maturation fluid coats the tissue and perfuses through the channels 638 into the output chamber 624, where the maturation fluid is removed through the port 640.

FIG. 8 is a perspective close-up view of an alternate embodiment 700 of the spherical pressure applicator 616' and piston cup 632' of FIG. 7. The apparatus is thus intended to mount within the vessel 602 of FIG. 7. Like parts are designated with like reference numerals plus a superscript prime. The spherical pressure applicator 616' has a shoulder portion 616A that abuts an annular flange 644. The flange is preferably affixed to the applicator element 616'. The flange in turn is sized to seat on an annular shoulder portion 648A of an annular stop ring 648. Specifically, the outermost diameter of the shoulder portion 616A is slightly greater than the outermost diameter of the stop flange 644 to enable vertical movement of the flange into and out of engagement with the stop ring 648. The spherical pressure applicator 616' has a lock nut 678 coupled to a top end portion to fixedly couple the applicator 616' to the shaft 614 of the apparatus.

The illustrated stop ring 648 has a central aperture that seats a plurality of guide rails 650 and locking seal elements 652. The stop ring 648 slidingly engages and moves about the guide rails 650 in a known manner. The seal elements 652 are further designed to lock the stop ring in place at a specified location. The location of the stop ring can define the downward most position of the pressure applicator 616' relative to the piston cup 632'. A tissue sheet 660 can be affixed to the top surface of the cup 632' such that it conforms with the contours of the concave surface feature 630'. The position of the stop ring 648 can be varied to adjust the gap size formed between the outermost region of the pressure applicator 616' and the concave surface feature 630'. The position of the these two elements relative to each other thus determines the type of force applied to the tissue 660. For example, the stop ring 648 can be positioned to form a gap between the applicator 616' and the tissue 660 to form shear forces when the fluid flows across the surface or when the applicator 616' is rotated. According to another practice, the stop ring can be positioned to enable the applicator to contact the tissue to apply a selected compressive force thereto. If the applicator 616' is rotated, it can also apply a frictional force to the tissue in the manner described in connection with FIG. 7.

The illustrated piston cup 632' includes a main body that is apertured with bores that mount one end of the guide rails 650. As shown, the guide rails 650 are mounted to both the piston cup 632' and the stop ring 648 to enable the stop ring to move relative to the piston cup. The tissue sheet 660 is secured to the top surface of the piston cup, and hence to the concave surface feature 630' by a pair of retaining ring assemblies. The assemblies include a pair of retaining rings 668 that are coupled together by a plurality of posts 670 mounted within corresponding apertures formed in the piston cup. The retaining rings and posts thus serve to hold the tissue sheet in place during the maturation process. A plurality of perfusion channels 638' are formed within the piston cup 632' and extend between the input and output chambers 622, 624.

A flexible annular diaphragm 670 is attached to the piston cup 632' by the retaining rings 668. The diaphragm extends between the piston cup and the inner wall of the housing 602, and is preferably attached to the housing to prevent fluid from leaking between the input and output chambers at locations other than the perfusion channels 638'.

In operation, the stop rings 648 are placed at selected locations to determine the separation or gap between the applicator 616' and the tissue 660. The maturation fluid 44 is then introduced to the input chamber 622 of the housing 602. The maturation fluid fills the input chamber and coats the tissue surface. The flexible diaphragm 670 prevents the maturation fluid from leaking to the output chamber around the piston cup 632'. The spherical pressure applicator 616 is placed at a selected position, the downward most position of which is defined by the stop ring location, to apply a selected shear or compression force to the tissue 660. For example, the applicator 616' can be vertically positioned within the housing 602 at any selected location. The applicator in particular can be lowered until the flange 644 abuts the shoulder 648A of the stop ring. The stop ring thus prevents the applicator from exceeding this downward most position. If the applicator is separated from the tissue by a predetermined amount, the applicator 616' can be rotated to create a shear force on the tissue 660. The tissue can undergo this maturation for a selected period of time and according to a predetermined treatment regimen. Those of ordinary skill will be readily able to determine the tissue maturation regimen in light of the type of tissue sheet, the type of maturation fluid, the type of any seeding cells, the expected replacement site, and other factors.

The spherical pressure applicator 616' can also be employed to apply a frictional force to the tissue sheet. For example, the stop ring 648 can be placed at a position that allows the applicator 616' to contact the surface of the tissue 660. The applicator in this position can apply a compressive of a selected degree based upon the amount of force applied normal to the tissue surface. The applicator 616' is then rotated to apply a frictional force to the entire tissue corresponding to the radius of curvature of the applicator 616' as it contacts the tissue mounted within the concave surface feature 630', which itself has a defined radius of curvature.

During tissue maturation, the maturation fluid coats the tissue and perfuses through the channels 638' into the output chamber, where the maturation fluid is removed through the housing port, FIG. 7.

The tissue construct employed in connection with the above-described tissue constructs can be either biopolymer fibers, biopolymer foams, or biopolymer mats. A more complete description of biopolymer tissue constructs suitable for use with the present invention is described below.

Fabrication of Biopolymer Foams

Many biopolymers can be formed into biocompatible foams, e.g., single or double density foams, composite foams, and biocompatible constructs which include biopolymer fibers, e.g., collagen fibers, biopolymer fabrics, e.g., collagen fabrics, and/or extracellular matrix particulate. As used herein, the term "foam" refers to a network of communicating microcompartments having biopolymer molecules and/or biopolymer filaments interspersed within the walls of the microcompartments. The biopolymer foams can be single density or double density foams. Double density foams have microcompartments that are smaller in volume, typically by a factor of approximately two to ten, than single density foams.

Examples of biopolymers which can be used to form a foam include collagen, alginic acid, polyvinyl alcohol, proteins, such as chondroitin sulfate, elastin, laminin, heparin sulfate, fibronectin and fibrinogen. A combination or mixture of one or more biopolymers can be used to form the biopolymer foams, and composite foams, i.e., combined single and double density foams, or combination of foams of different biopolymers, that can form the biopolymer constructs of the invention. For example, a combination of chondroitin sulfate and fibronectin can be used to form biopolymer fibers that can be incorporated with a biopolymer foam to form a biopolymer construct described herein. A preferred biopolymer is collagen.

The biopolymers foams, e.g., single or double density foams, can be formed into structures of any form or shape, e.g., strips, sheets, tubes, etc. Structures comprising biopolymer foams combined with polymer mesh, e.g., a Teflon mesh are possible. Biopolymer foams can be used with tissue culture inserts for multiple plates which can be used as molds in which foams and biopolymer constructs of the invention can be formed for cell culture. Polymer meshes used with the foams and foam compositions of the invention can expose cells contained on and within the foams and foam compositions to the atmosphere as, for example, when the foams and foam compositions are used as skin equivalents to stimulate formation of a stratum corneum. Both the meshes and culture inserts have the advantage of providing a means for handling the foams and foam compositions without requiring actual contact with the foams or foam compositions. The shaped structures into which the foams and foam compositions are made can mimic those of tissues or body parts to be replaced and thus can be used as prostheses or grafts which tissue cells remodel to promote regeneration of a replacement tissue in the recipient. Extracellular matrix particulates and/or viable cells can also be added to the biopolymers to further promote cell in growth and tissue development and organization within the foams.

Biopolymer foams can be produced by forming a biopolymer solution, freeze-drying the solution to form a biopolymer foam, and crosslinking the biopolymer foam. Alternatively, the foam can be formed by performing the crosslinking step prior to the freeze-drying step. The step of freeze-drying converts the biopolymer solution into a foam, i.e., a network of communicating microcompartments with biopolymer molecules and/or filaments interspersed throughout its walls. When the foam is crosslinked, it becomes physically stable and insoluble in aqueous solutions. Preferably, the biopolymer solution is polymerized, prior to freeze-drying, to form a biopolymer lattice. As used herein, a biopolymer lattice refers to a network of biopolymer filaments in which fluid is trapped. Biopolymer filaments are nanometer-sized forms of polymerized biopolymer molecules. For example, if the biopolymer is collagen, the collagen polymerizes into nanometer sized filaments by a process of self-assembly.

The biopolymer solution can be formed by treating the biopolymer in such a manner that it becomes soluble, e.g., by manipulating its pH to put it into solution, can be polymerized using methods of polymerization known in the art. For example, the biopolymer, e.g., collagen, can be polymerized to form a biopolymer lattice by manipulation of the pH of the biopolymer solution, e.g., by exposure to ammonium vapor or by adding base. As the pH of the solution reaches neutrality, the biopolymer polymerizes. The rate of polymerization is proportional to temperature and can be controlled by regulating the temperature of the collagen solution.

After the biopolymer has been polymerized to form a biopolymer lattice, it is typically freeze-dried and/or crosslinked. Typically, the order of the these steps depends on the method of crosslinking used. For example, if the crosslinking method is a liquid phase method, e.g., the use of aldehydic crosslinking methods, the crosslinking step is performed prior to the freeze-drying step. Alternatively, if the crosslinking method is a solid phase method, e.g., use of ultraviolet radiation, the crosslinking step is performed after the freeze-drying step. Crosslinking of the biopolymer can be accomplished by use of crosslinking methods known in the art. For example, the biopolymer can be crosslinked by subjection to ultraviolet radiation or by treatment with chemical crosslinking agents such as carbodiimide, glutaraldehyde, acetaldehyde, formaldehyde, and ribose. The biopolymer can also be crosslinked by dehydrothermal crosslinking.

If desired, prior to freeze-drying, selected reinforcing material can be added to the biopolymer solutions. Such reinforcing materials include biopolymer fibers, threads, e.g., woven or braided threads, and/or fabrics, e.g., non-woven fabrics, prepared, for example, by textile methods. Biopolymer threads, e.g., collagen threads, can be prepared by extruding the biopolymer in solution into a coagulation bath and transferring the biopolymer to a bath containing ethanol or acetone or another dehydrating solution. Alternatively, the thread can be dehydrated by subjection to vacuum-drying. The biopolymer thread can then be crosslinked by, for example, methods described herein. An example of an apparatus for spinning and processing a biopolymer fiber, e.g., collagen fiber, is described in U.S. Ser. No. 08/333,414, filed Nov. 2, 1994, the contents of which are incorporated herein by references in their entirety. The threads can then be dried, spooled, for example, by pulling the moving thread over more rollers, stretching and drying it and then winding it onto spools. The threads can be woven or braided into fabric or other complex forms or constructs for use as described herein.

The term biopolymer fabrics is intended to include nonwoven biopolymer fabrics, are typically composed of a mat of entangled biopolymer fibers of a selected size and density. Typically, the nonwoven biopolymer fabrics are produced by spooling dry biopolymer fiber onto a drum of circumference equal to that of the length of an individual fiber element. Spooling is continued until the number of wraps of fiber on the drum equals the number of pieces of fiber required for the fabric. A cut is then made across the wound fiber in a direction parallel to the drum axis and the fibers are removed from the drum. A textile machine, such as a staple length cutter can be used to cut the fibers to a selected length. The fiber can then be crosslinked if it has not been previously crosslinked. The fiber is then dispersed in a volume of a phosphate buffer solution for a period of time to decrease its pH and soften the fiber. The fiber is transferred to a volume of water and agitated mechanically to produce entanglement of the fiber strands. The entangled fiber strands are sieved from the water onto a collection screen until they coat the screen in a mat of uniform density. The mat is then dried on the screen or dried after transfer to another surface, screen, or cell culture device. If desired, the nonwoven mat can be cut or punched into smaller shapes after drying.

The biopolymer solution can then be freeze-dried to form a foam. The freezing step can be a controlled freezing step performed according to the method described in U.S. Pat. No. 4,531,373, the contents of which are incorporated herein by reference. The freeze-drying cycle typically includes freezing, evacuation, and drying phases. The freezing temperatures suitable for formation of the biopolymer foams of the invention depend upon the concentration of the biopolymer in solution or in the biopolymer lattice. Thus, for a collagen lattice in which the collagen is at a concentration of about 5 mg/ml the freezing temperature is typically less than $-26°$ C. The collagen lattice is exposed to this temperature for a period of about 1 hour. A vacuum is then applied to the collagen lattice as the temperature is slowly raised.

To prevent the formation of fissures in the foam and thus to allow for greater foam size, an anti-freeze polypeptide (AFP) or an anti-freeze glycoprotein (AFGP) can be added to the biopolymer solution prior to or during the freezing step. Examples of AFPs include the AFPs which belong to the AFP Types I, II, and III. For a detailed description of the different types of AFPs, see, e.g., U.S. Pat. No. 5,358,931, PCT publication WO 92/12722, and PCT publication WO 91/10361, the contents of which are incorporated herein by reference. These polypeptides and glycoproteins prevent the formation of large ice crystals during freezing of the biopolymer solution and also prevent the formation of crystals of recrystallization during the drying process. Large ice crystals can create fissures in the resulting foam which contribute to poor crosslinking and splitting of the foam. Use of AFPs and AFGPs allow for the formation of a pore structure which has connected channels and thus allows for cohesion of the various sections of the foam. This feature improves the quality of the foams and enables the production of large foams. For example, when an AFP or combination of AFPs is freeze-dried with the biopolymer in high concentrations, e.g., about 0.2 to 0.5 mg/ml (about 124 $\mu$M), it dramatically reduces the normal foam pores until the foam resembles tightly packed long fibers. The foams produced using the AFPs in the freezing cycle can be employed, for example, as implants which direct specific cellular processes, e.g., through growth along the fibers.

After a single density foam is freeze-dried, it can be hydrated with, for example, a sterile aqueous buffer. If the hydrated single density foam is to be further shaped to have a selected form, e.g., it can be molded or formed in, on, or around a desired shape, e.g., it can be molded around a mandrel to form a tubular shape. Typically foams are then dried, e.g., air dried, at a temperature not greater than about $37°$ C.–$40°$ C. under sterile conditions. At temperatures greater than about $37°$ C., the biopolymer in the foams will begin to denature, resulting in a double density foam that retains the fibers, walls, and two dimensional shape, but not the microcompartment sizes of the single density foams. The double density foam is stiff when dry and pliable when wet. It is resistant to tearing and to enzymatic digestion to a much greater extent that the single density foam. In contrast to the single density foam, the double density foam is a tight matrix which is preferred as a substrate for cells which normally grow on surfaces such as epithelial cells and endothelial cells. For example, the double density foam can be formed in the shape of a tube for use in reconstructing vessels or ducts or into a sheet and secured to large areas with sutures. Alternatively, the double density foam can be seeded with mesenchymal cells such as fibroblasts, muscle cells, chondrocytes, etc.

The resultant foam, whether single or double density, is removed, according to the invention, from support or shaping structures with which it is intimate contact and to which it typically adheres.

Fabrication of Collagen Matts

The present invention contemplates the maturation of biopolymer scaffolds in the form of biopolymer matt or biopolymer matt composites, e.g., resorbable biopolymer matt, for membranous or thick tissue applications, or as a filler material for tissue repair and tissue reconstruction which has a high strength to unit volume even before crosslinking. The invention also features biopolymer matt compositions comprising biopolymer matt and various layers of biopolymer foams, biocompatible constructs comprising biopolymer matt and extracellular matrix macromolecules, and methods for making and using the biopolymer matt, biopolymer matt composites, biopolymer matt compositions, and biocompatible matt constructs.

The biopolymer matt and biopolymer matt compositions can be used in vitro, for example, as model systems for research, or in vivo as prostheses or implants to replace damaged or diseased tissues or to provide scaffolds which, when occupied by cells, e.g., host cells, are remodeled to become functional tissues. In either case, the matt, matt composites, and matt compositions can be seeded with cells, e.g., mammalian cells, e.g., human cells, of the same type as those of the tissue which the matt, matt composites, or matt compositions is used to repair, reconstruct, or replace. Examples of tissues which can be repaired and/or reconstructed using the matt, matt composites, and matt compositions described herein include nervous tissue, skin, vascular tissue, cardiac tissue, pericardial tissue, muscle tissue, ocular tissue, periodontal tissue, connective tissue such as bone, cartilage, tendon, and ligament, organ tissue such as kidney tissue, and liver tissue, glandular tissue such as pancreatic tissue, mammary tissue, and adrenal tissue, urological tissue such as bladder tissue and ureter tissue, and digestive tissue such as intestinal tissues. For example, the matt, matt composites, and matt compositions seeded with tissue specific cells are introduced into a recipient, e.g., a mammal, e.g., a human. Alternatively, the seeded cells which have had an opportunity to organize into a tissue in vitro and to secrete tissue specific biosynthetic products such as extracellular matrix proteins and/or growth factors which bond to the matt and matt compositions are removed prior to implantation of the matt or matt compositions into a recipient.

The present invention can utilize biopolymer matts, biopolymer matt composites, biopolymer matt compositions comprising biopolymer matt and biopolymer foam, biocompatible constructs comprising biopolymer matt and extracellular matrix macromolecules, and methods for making and using the matt, matt composites, and matt compositions. The biopolymer matt, matt composites, and matt compositions, in their native fibril structure, contain information to induce the repair or regeneration of damaged, diseased or missing tissue. Additional information for repair or regeneration can be added by mixing other informational macromolecules to the biopolymer matt, matt composites, and matt compositions. The biopolymer matt, matt composites, and matt compositions are fully resorbable when not reinforced by non-resorbable fibers and over time can be replaced by new normal pure host tissue. The biopolymer matt, matt composites, and matt compositions are more resistant to enzymatic breakdown than other collagen products of high information content, such as gels or foams. The biopolymer matt, matt composites, and matt compositions can be produced under physiological conditions, so living cells can be incorporated throughout the structure and on the completed form, thus yielding a living implant. The information content of the biopolymer matt, matt composites, and matt compositions can induce authentic healing and repair. For example, a living cell matt can replace the missing host tissue and its function immediately, and still be remodeled by authentic host tissue gradually with no interruption of tissue function. The biopolymer matt, matt composites, and matt compositions can be produced in a manner which gives them more strength than other collagen products of high information content. Therefore, they can be used in situations which requires an implant of strength.

A biopolymer is a naturally occurring polymeric substance formed from individual molecules in a biological system or organism. Biopolymers can also be man-made by manipulation of the individual molecules once obtained outside the biological system or organism. The biopolymer is suitable for introduction into a living organism, e.g., a mammal, e.g., a human. The biopolymer is non-toxic and bioabsorbable when introduced into a living organism and any degradation products of the biopolymer should also be non-toxic to the organism. The biopolymers of the invention can be formed into biocompatible forms, e.g., matt, matt composites, matt compositions, including biocompatible foams, biocompatible gels, biocompatible constructs which include biocompatible fibers, e.g., collagen fibers, biocompatible fabrics, e.g., collagen fabrics, all with or without other extracellular matrix macromolecules. Examples of molecules which can form biopolymers and which can be used in the present invention include collagen, laminin, elastin, fibronectin, fibrinogen, thrombospondin, gelatin, polysaccharides, poly-1-amino acids and combinations thereof. In one embodiment, a combination or mixture of one or more biopolymers can be used to form the biocompatible forms, e.g., fibers, matt, and matt compositions of the invention. For example, a combination of laminin and type IV collagen can be used to form the biopolymer fibers described herein. A preferred molecule for biopolymer production is collagen.

Preferred sources of molecules which form biopolymers include mammals such as pigs, e.g., near-term fetal pigs, sheep, fetal sheep, cows, and fetal cows. Other sources of the molecules which can form biopolymers include both land and marine vertebrates and invertebrates. In one embodiment, the collagen can be obtained from skins of near-term, domestic porcine fetuses which are harvested intact, enclosed in their amniotic membranes. Collagen or combinations of collagen types can be used in the matt and matt compositions described herein. Examples of collagen or combinations of collagen types include collagen type I, collagen type II, collagen type III, collagen type IV, collagen type V, collagen type VI, collagen type VII, collagen type VIII, collagen type IX, collagen type X, collagen type XI, collagen type XII, collagen type XIII, and collagen type XIV. A preferred combination of collagen types includes collagen type I, collagen type III, and collagen type IV. Preferred mammalian tissues from which to extract the molecules which can form biopolymer include entire mammalian fetuses, e.g., porcine fetuses, dermis, tendon, muscle and connective tissue. As a source of collagen, fetal tissues are advantageous because the collagen in the fetal tissues is not as heavily crosslinked as in adult tissues. Thus, when the collagen is extracted using acid extraction, a greater percentage of intact collagen molecules is obtained from fetal tissues in comparison to adult tissues. Fetal tissues also include various molecular factors which are present in normal tissue at different stages of animal development.

In a preferred embodiment, the biopolymer matt, matt composite, or matt composition is a collagen matt, collagen matt composite, or collagen matt composition. Collagen solutions can be produced by salt extraction, acid extraction, and/or pepsin extraction from the starting material. In a preferred embodiment, the collagen used is produced by sequentially purifying two forms of collagen from the same collagen-containing starting material. First, intact collagen is acid extracted from the starting material, the extract is collected and collagen is prepared as a collagen solution, e.g., by precipitating the collagen with sodium chloride and solubilizing the collagen in a medium having an acidic pH. Meanwhile, truncated collagen, i.e., collagen from which the telopeptides have been cleaved or partly cleaved leaving only the helical portion or the helical portion with some telopeptides, is extracted from the starting material using enzyme, e.g., an enzyme which is functional at an acidic pH, e.g., pepsin, extraction. Then, the collagen from this pepsin extract is purified separately by similar methods as from the first extract.

The biopolymer matt can also include a densely packed random array of biopolymer fibrils and has a high strength to unit volume and preserves the native structure of the biopolymer fibrils. Examples of molecules which can form biopolymer fibrils which can be used in the biopolymer matt include collagen, laminin, elastin, fibronectin, fibrinogen, thrombospondin, gelatin, polysaccharides, poly-1-amino acids and combinations of biopolymers. A preferred molecule for biopolymer production is collagen, e.g., porcine fetal collagen. In other embodiments, the biopolymer matt can include macromolecules necessary for cell growth, morphogenesis, differentiation, or tissue building and combinations thereof, extracellular matrix particulates and/or cells.

The biopolymer matt, matt composite, or matt composition can be conditioned with cells prior to use in vitro or in vivo. Cell conditioning is an application-specific method used to speed integration of the matt, matt composite, or matt composition into its new function, to speed recovery of repair tissue and to direct authentic replacement of the damaged or missing tissue. Biopolymer matt, biopolymer matt composites, or biopolymer matt compositions can be used as a substrate for the growth of cells appropriate for the site of use. For example, for a biopolymer matt, biopolymer matt composite, or biopolymer matt composition used to repair bone defects as a periosteum, the conditioning cells would include, e.g., osteoblasts. For a biopolymer matt, biopolymer matt composite, or biopolymer matt composition used as pericardial membrane, the conditioning cells would include, e.g., mesothelial cells. For a biopolymer matt, biopolymer matt composite, or biopolymer matt composition used in the abdomen, the conditioning cells would include, e.g., mesothelial cells.

During conditioning, cells residing on biopolymer matt, biopolymer matt composite, or biopolymer matt composition deposit onto the matt, matt composite, or matt composition, macromolecules, such as protein products recognizable by the cells neighboring the defect at the site of matt, matt composite, or matt composition placement. The cell choice and thus the protein products can direct two things. They can direct the migration of the neighboring cells onto the matt, matt composite, or matt composition and the remodeling of the matt, matt composite, or matt composition material to replace the matt, matt composite, or matt composition with authentic covering tissue or the cell products will stimulate the regrowth of the tissue desired beneath the matt, matt composite, or matt composition while other cells remodel the matt, matt composite, or matt composition from the opposite side. After a period of time for the conditioning cells to deposit sufficient signaling and extracellular matrix molecules onto the matt, matt composite, or matt composition, the matt, matt composite, or matt compositions can be used as living implants to serve as living tissue equivalents or model tissue systems. Alternatively, cells of the matt, matt composite, or matt compositions can be killed by freezing or freeze drying the construct. Freeze drying eliminates living material, but leaves the deposited proteins in their natural states.

The biopolymer matt can be used alone, e.g., as a collagenous membrane for a periodontal barrier, or as a periosteal barrier to aid in bone repair. The biopolymer matt can also be used as a biopolymer composite by collecting sequential layers of different fibril slurry on the porous support and fusing these layers to each other. The biopolymer matt or biopolymer matt composites can also be used as a matt composition comprising a biopolymer matt and a biopolymer foam, e.g., as in the tissue repair of dura mater of the central nervous system. For example, a single density foam can be cast onto a finished matt to yield a structure with two layers of distinct characteristics, the matt layer of high density and low to no porosity and the foam layer with low density and high porosity. Single and double density biopolymer foams are described in U.S. Ser. No. 08/754,818, filed Nov. 21, 1996, the contents of which are incorporated herein by references in their entirety. Such implant sites consisting of compound tissue can be treated with matt compositions which include epi-meso- or endothelial cells on a matt surface and mesenchymal cells in the foam scaffold. For these applications, the low porosity matt side can minimize adhesions or fluid loss on one surface and the high porosity side can attract and support cell growth and differentiation required for healing. To further protect against adhesions or fluid loss in these applications and in applications requiring the use of matt alone, one can modify the surface of the matt. Modification can be accomplished biologically by growing and differentiating keratinocytes on one side of the matt to produce a stratum corneum. Matt compositions comprising one or more layers of biopolymer matt or biopolymer matt composites and more than one layer of single or double density biopolymer foams are also specifically contemplated herein.

As mentioned above, the matt can incorporate fiber structures, such as a single fibers, braids, or fabrics to achieve general reinforcement, directed reinforcement or to achieve directional cell growth. Examples of implants requiring such structures include skeletal replacements or temporary reinforcing structures. The matt can be cast in shapes other than sheets. It can be cast as tubes or orbs, such as spheres, to produce membranous structures which can contain material or liquids for specialized functions. Examples of implants made from matt, matt composite, or matt compositions include, for example, vessels, ducts, ureters, bladders and bone implants from matt cylinders filled with bone replacement material.

A matt composition comprising a matt and a single density foam, either with or without cell seeding, which is not freeze dried, can be used to build living tissue equivalents or model tissue systems. An example of this is the growth of dermal fibroblasts in the single density foam and the differentiated growth of keratinocytes on the porous surface matt layer for a skin model or a living implant system which quickly replaces lost function in critical situations and which can be cryopreserved for storage stockpiling. If not desired as a living implant system, the cell-laden developed complex can be freeze dried for later use as an implant which directs host tissue regrowth through information derived from the material the cultivated cells deposit onto the structures prior to freeze drying.

The biopolymers can be used to create matts, matt composites, or matt compositions which can be in any form or shape, e.g., strips, sheets, tubes, etc. In addition, the biopolymers can be used to create matts which can be supported by polymer mesh, e.g., a Teflon mesh, or used with tissue culture inserts for multiwell plates which can be used as molds in which matt, matt composites, and matt compositions of the invention can be formed on the polycarbonate membrane of the insert. Polymer meshes used with the matt, matt composites, and matt compositions of the invention can expose cells contained on and within the matt, matt composites, and matt compositions to the atmosphere as, for example, when the matt, matt composites, and matt compositions are used as skin equivalents to stimulate formation of a stratum corneum. Both the meshes and culture inserts have the advantage of providing a means for handling the matt, matt composites, and matt compositions without requiring actual contact with the matt, matt composites, or matt compositions. The forms and shapes in which the matt, matt composites, and matt compositions are made can mimic those of tissues or body parts to be replaced and thus can be used as prostheses or grafts which tissue cells remodel to promote regeneration of a replacement tissue in the recipient.

Macromolecules necessary for cell growth, morphogenesis, differentiation, and tissue building can also be added to the biopolymer molecules or to the biopolymer fibrils to further promote cell ingrowth and tissue development and organization within the matt. The phrase "macromolecules necessary for cell growth, morphogenesis, differentiation, and tissue building" refers to those molecules, e.g., macromolecules such as proteins, which participate in the development of tissue. Such molecules contain biological, physiological, and structural information for development or regeneration of the tissue structure and function. Examples of these macromolecules include, but are not limited to, growth factors, extracellular matrix proteins, proteoglycans, glycosaminoglycans and polysaccharides. Alternatively, the biopolymer matts, matt composites, and matt compositions of the invention can include extracellular matrix macromolecules in particulate form or extracellular matrix molecules deposited by cells or viable cells.

As used herein, the term "matt" refers to a biopolymer scaffold comprising a densely packed random array of biopolymer fibrils or bundles of fibrils or particles, e.g., collagen fibrils. Matts which have been dried, as discussed previously, possess a wet tensile strength of at least 0.02 MPa with a preferred strength of greater than 1 MPa and have a collagenase resistance of at least 20 min per mg of collagen at a collagenase concentration of 10 units per 1 cm$^2$ of product. Typically the fibrils or bundles of fibrils are between about 0.01 $\mu$m and 50 $\mu$m in diameter and between about 0.0002 and 5.0 mm in length, preferably 0.1 $\mu$m to 20 $\mu$m wide and 0.01 mm to 3 mm long. Matts, whether dried or not, possess the following characteristics: (1) physically stable in aqueous solutions; (2) nontoxic to living organisms; (3) can serve as a substrate for cell attachment and growth; (4) approximately 0.01 mm to 20 mm thick, preferably 0.1 to 5.0 mm thick.

As used herein, the term "fibrils" refers to ordered multimers of molecules which create a fibrous overall structure. In the case of collagen fibrils, the collagen molecules are arranged in a quarter stagger, where each side-by-side association of molecules has an orderly shift of 25% (the head of one collagen molecule is arranged to be juxtaposed to the adjacent molecule 25% down the chain of that molecule). Fibrils, especially those of collagen often have a characteristic appearance by electron microscopy. Fibrils associate into bundles. Higher multiples of fibril bundles are fibers.

The term "matt composite" refers to a biopolymer form comprising sequential layers of biopolymer matt which are bonded to each other.

The term "matt composition" refers to a biopolymer composition comprising a matt, e.g., a biopolymer matt which is preferably resorbable, and optionally, one or more biopolymer foams, e.g., a single or double density foam. Single and double density biopolymer foams are described in U.S. Ser. No. 08/754,818, filed Nov. 21, 1996, the contents of which are incorporated herein by references in their entirety.

The biopolymer foams can be single density or double density foams. As used herein, the term "foam" refers to a network of communicating microcompartments having biopolymer molecules and/or biopolymer filaments interspersed within the walls of the microcompartments. The language "single density foam" refers to a biopolymer foam having at least two of the following characteristics: 1) it has microcompartments with the volume dimensions of x, y, and z wherein x=length, y=width, and z=height and are substantially equal. Typically, x, y, and z range from about 1 $\mu$m to about 300 $\mu$m, preferably from about 20 $\mu$m to about 200 $\mu$m, more preferably from about 40 $\mu$m to about 150 $\mu$m, and most preferably from about 50 $\mu$m to about 100 $\mu$m; 2) it has microcompartments with an average wall thickness of less than about 10 $\mu$m; 3) it has microcompartments with walls which include biopolymer fibers and/or filaments; 4) it is physically stable in aqueous solutions; 5) it is nontoxic to living organisms; and 6) it can serve as a substrate for cell attachment and growth. The single density foams retain their structure when hydrated, for example, in aqueous buffer solution or tissue culture medium. In addition, the three dimensional structure of the single density foams can support the organization of cells seeded into them. Single density foams, when prepared from collagen and without cells, can be readily digested with collagenase, e.g., 0.1% collagenase. Examples of molecules which can form biopolymers which can be used in the single density biopolymer foams include collagen, alginic acid, polyvinyl alcohol, elastin, chondroitin sulfate, laminin, fibronectin, fibrinogen, and combinations of these biopolymers. A preferred biopolymer is collagen, e.g., porcine fetal collagen. In other embodiments, the single density biopolymer foams can include extracellular matrix particulates and/or cells.

As used herein, the language "double density foam" refers to a biopolymer foam having at least two of the following characteristics: 1) it has microcompartments with the volume dimensions of x, y, and z wherein x=length, y=width, and z=height, two of which are substantially equal and the third of which is decreased or diminished by a factor of at least about 10, and more preferably at least about 20 or more compared to the same dimension in the single density foam, and can range from about 1 $\mu$m to about 300 $\mu$m, preferably from about 20 $\mu$m to about 200 $\mu$m, more preferably from about 40 $\mu$m to about 150 $\mu$m, and most preferably from about 50 $\mu$m to about 100 $\mu$m; 2) it has microcompartments with an average wall thickness of less than about 10 $\mu$m; 3) it has microcompartments with walls which include biopolymer fibers and/or filaments; 4) it is physically stable in aqueous solutions; 5) it is nontoxic to living organisms; and 6) it can serve as a substrate for cell attachment and growth. The double density foams, when prepared from collagen, are resistant to collagenase digestion to a greater degree than single density foams made from collagen, e.g., from about 3 to about 5 times or more, more resistant to 0.1% collagenase than single density foams. Double density foams prepared from collagen also have a higher collagen density per unit volume than the collagen content per unit volume of single density foams. When hydrated, the height of the double density foams is typically from about 0.2 mm to about 0.4 mm. Either surface of the double density foam provides a substrate suitable for plating epithelial, endothelial, and mesothelial cells which can form sheets. Mesenchymal cells can also be seeded onto the double density foams. The double density foams can be produced in the same sizes and same forms, e.g., in any form and in combination and bonded to a polymer mesh or as a multiwell plate insert, as the single density foams. Cells grown on both the single and double density foams of the invention have morphologies characteristic of cells of three dimensional tissues and can form normal intercellular relationships, i.e., intercellular relationships like those in the tissue from which they are derived or obtained. Preferred biopolymers for use in double density foams are described above as in single density foams. In other embodiments, the double density biopolymer foams can include extracellular matrix particulates and/or cells.

Either the surface of the matt, matt composites, or matt compositions can provide a substrate suitable for plating epithelial, endothelial, and mesenchymal cells which can be formed into sheets or other articles. Cells can also be seeded onto single or double density foams. Cells grown on biopolymer matts and biopolymer matt compositions have morphologies characteristic of cells of three dimensional tissues and can form normal intercellular relationships, i.e., intercellular relationships like those in the tissue from which they are derived or obtained.

Biopolymer nonwoven fabrics are typically composed of a collection of entangled biopolymer fibers of a selected size and density. Typically, the nonwoven biopolymer fabrics are produced by spooling dry biopolymer fiber onto a drum of circumference equal to that of the length of an individual fiber element. Spooling is continued until the number of wraps of fiber on the drum equals the number of pieces of fiber required for the fabric. A cut is then made across the wound fiber in a direction parallel to the drum axis and the fibers are removed from the drum. The fiber can then be crosslinked if it has not been previously crosslinked. The fiber is then dispersed in a volume of a phosphate buffer solution for a period of time to decrease its pH and soften the fiber. The fiber is transferred to a volume of water and agitated mechanically to produce entanglement of the fiber strands. The entangled fiber strands are sieved from the water onto a collection screen until they coat the screen in a mat of uniform density. The nonwoven fabric is then dried on the screen or after transfer to another surface, screen, or cell culture device. If desired, the nonwoven mat can be cut or punched into smaller shapes after drying.

Examples of materials suitable for matt reinforcing fibers, threads, braids, bundles of fibers, fabrics and/or nonwovens are materials which form biopolymers, resorbable polymers and non-resorbable polymers. Materials for biopolymers include collagen, alginic acid, laminin, elastin, gelatin, fibronectin, fibrinogen, thrombospondin, polysaccharides, poly-1 amino acids and combinations thereof. Materials for resorbable polymers include poly-α-hydroxyesters such as poly-1-lactic acid and poly-1-glycolic acid, polydioxinone, polyvinyl alcohol, surgical gut and combinations thereof. Examples of materials for non-resorbable polymers include silk, nylon, polytetrafluoroethylene, polypropylene, polyesters, polyurethanes and combinations thereof. Further combinations for fibers can be made by casting resorbable polymer fibers on non-resorbable polymers or casting biopolymer fibers on resorbable or nonresorbable fibers. A preferred material is collagen, preferably fetal porcine collagen.

Examples of implants requiring such reinforced structures include skeletal replacement, hernia repair or temporary reinforcing structures. For example, to repair a rotator cuff, strong fibers or sutures, preferably resorbable sutures, can be embedded within the matt structure at the time of depositing the fibril slurry to enable high tension to be placed on the finished product in the direction of reinforcement. These structures are described further herein.

Biocompatible constructs which include biopolymer matt or biopolymer matt compositions of the invention and extracellular matrix macromolecules are also specifically contemplated herein. Extracellular matrix macromolecules in soluble or particulate form dispersed or suspended in a biopolymer solution can also be applied onto and/or into the matt and matt compositions of the invention, thereby forming a matt, matt composite, or matt composition having extracellular matrix macromolecules or particulates. As used herein, the language "particulate form of extracellular matrix" refers to a fragment of an extracellular matrix derived from a tissue source formerly having living cells but which has been processed to remove the cells and to retain noncellular extracellular matrix factors such as, for example, growth factors also proteins, proteoglycans, glycosaminoglycans necessary for cell growth, morphogenesis, and differentiation. Methods for forming extracellular matrix particulates for producing graft tissue are disclosed in U.S. patent application Ser. No. 07/926,885, filed Aug. 7, 1992, U.S. patent application Ser. No. 08/302,087, filed Sep. 6, 1994, and U.S. patent application Ser. No. 08/471,535, filed Jun. 6, 1995. The teachings of U.S. patent application Ser. Nos. 07/926,885, 08/302,087, and 08/471,535 are incorporated herein by reference.

The methods for forming extracellular matrix particulates include freezing a tissue source, e.g., a connective tissue source, having living cells, whereby the living cells are disrupted to form cell remnants consisting of, for example, cytoplasmic and nuclear components. The tissue source is then processed, e.g., by grinding, washing and sieving, to remove the cytoplasmic and nuclear components without removing extracellular matrix including macromolecules necessary for cell growth, migration, differentiation, and morphogenesis. The extracellular matrix is freeze-dried and fragmented, e.g., cryomilled to produce particulates of defined sizes, to produce extracellular matrix particulates.

The extracellular matrix particulates can include extracellular matrix proteins. For example, extracellular matrix particulates obtained from skin include transforming growth factor β1, platelet-derived growth factor, basic fibroblast growth factor, epidermal growth factor, IGFI, bFGF, syndecan-1, decorin, fibronectin, collagens, laminin, tenascin, and dermatan sulfate. Extracellular matrix particulates from lung include PDGF, TGFβ1, bFGF, VEGF, syndecan-1, fibronectin, laminin, and tenascin. The extracellular matrix particulates can also include cytokines, e.g., growth factors necessary for tissue development. The term "cytokine" includes but is not limited to growth factors, interleukins, interferons and colony stimulating factors. These factors are present in normal tissue at different stages of tissue development, marked by cell division, morphogenesis and differentiation. Among these factors are stimulatory molecules that provide the signals needed for in vivo tissue repair. These cytokines can stimulate conversion of an implant into a functional substitute for the tissue being replaced. This conversion can occur by mobilizing tissue cells from similar contiguous tissues, e.g., from the circulation and from stem cell reservoirs. Cells can attach to the prostheses which are bioabsorbable and can remodel them into replacement tissues.

The matt, matt composite, and matt compositions can also be used as prostheses which can be introduced or grafted into recipients, e.g., such as mammalian recipients, e.g., humans. For example, the matt, matt composites, and matt compositions can be used as a prosthesis or to reconstitute, for example, the following types of tissue: nervous tissue, skin, vascular tissue, muscle tissue, connective tissue such as bone, cartilage, tendon, and ligament, kidney tissue, liver tissue, and pancreatic tissue. Tissue cells seeded into the matt, matt composites, and matt compositions can be obtained from a mammal, e.g., a human. If not added during matt formation, tissue cells are delivered to the matt, matt composites, and matt compositions by first suspending the cells in small volumes of tissue culture medium. The tissue culture medium which contains the cells can then be applied in drops to the matt, matt composites, or matt compositions. Alternatively, the matt, matt composites, or matt compositions can be placed in a vessel which contains the tissue culture medium and cells in suspension and which shakes such that the tissue culture medium containing the cells is distributed throughout the matt, matt composites, or matt compositions. In another embodiment, tissue cells can be suspended in a biopolymer solution e.g., a collagen solution, at low concentrations, at a temperature of about 4° C. to 10° C., and at a pH of about 7.0. The solution containing the cells can then be delivered to the matt, matt composites, and matt compositions. As matt is warmed to 37° C., the biopolymer solution, e.g., collagen solution, forms a gel in the matt. As used herein, the term "gel" refers a network or mesh or biopolymer filaments together with an aqueous solution trapped within the biopolymer scaffold of biopolymer fibrils. An alginate gel for use as a delivery vehicle of cells to the matt, matt composites, or matt compositions of the invention can be produced by addition of calcium which causes polymerization at room temperature and at a neutral pH. Selected epithelial, endothelial, or mesothelial cells can then be plated onto the surface of the gel-filled matt, matt composite., or matt composition.

The biopolymer matt can be used alone, e.g., as a collagenous membrane for a periodontal barrier, or as a periosteal barrier to aid in bone repair. Alternatively, the biopolymer matt can be used in a biopolymer matt composition comprising a biopolymer matt and a biopolymer foam, e.g., as in the tissue repair of dura mater of the central nervous system, e.g., a single density foam can be cast onto the finished matt to yield a structure with two layers of distinct characteristics, the matt layer of high density and low to no porosity and the foam layer with low density and high porosity. Single and double density biopolymer foams are described in U.S. Ser. No. 08/754,818, filed Nov. 21, 1996, the contents of which are incorporated herein by references in their entirety. Implant sites requiring a compound tissue, e.g., skin made up of two tissues, the epidermis and the dermis, can be treated with matt compositions which include epi- meso- or endothelial cells on a matt surface and mesenchymal cells in the foam scaffold. For these applications, the low porosity matt side can minimize adhesions or fluid loss on one surface and the high porosity side can attract and support cell growth and differentiation required for healing. Modification can be accomplished, for example, biologically by growing and differentiating keratinocytes on one side of the matt to produce a stratum corneum. Matt compositions comprising one or more layers of biopolymer matt or biopolymer matt composites and more than one layer of single or double density biopolymer foams are also specifically contemplated herein.

As mentioned above, the matt can incorporate fiber structures, such as a single fibers, braids, bundles of fibers or fabrics to achieve general reinforcement, directed reinforcement or to achieve directional cell growth. Examples of implants requiring such structures include, e.g., skeletal replacements or temporary reinforcing structures.

The matt, matt composites, or matt compositions can be cast in shapes other than sheets. It can be cast as tubes or orbs, such as spheres, to produce membranous structures which can contain material or liquids for specialized functions. Examples of implants made from matt, matt composites, or matt compositions include, e.g., vessels, ducts, ureters, bladders and bone implants from matt cylinders filled with bone replacement material. As used herein, the term "bone replacement material" refers to material which can fill voids in bone and which can assist in bone repair. Examples of bone replacement material include, but are not limited to, autologous bone graft, bone powder, demineralized bone, calcium sulfates, and calcium phosphates, e.g., hydroxyapatites, brushites and octacalcium phosphate. A matt composition comprising a matt and a single density foam, either with or without cells, and which is not dried can be used to build living tissue equivalents or model tissue systems. An example of this is the growth of dermal fibroblasts in the single density foam and the differentiated growth of keratinocytes on the porous surface matt layer for a skin model or a living implant system which quickly replaces lost function in critical situations and which can be cryopreserved for storage stockpiling. If not desired as a living implant system, the cell-laden developed complex can be freeze dried for later use as an implant which directs host tissue regrowth through information derived from the material the cultivated cells deposit onto the structures prior to freeze drying as described for cell conditioning above.

The matt, matt composites, and matt compositions of the invention can also be formed into vascular prostheses in the form of a tube and can be seeded internally with smooth muscle cells delivered in a neutralized collagen solution that gels after delivery, externally with adventitial fibroblasts and on its luminal surface with endothelial cells. For example, a tubular matt can be formed by dispensing biopolymer fibril slurry into a tube whose inner diameter is the outer diameter of the desired matt. The tube is rolled continuously while the slurry dries. While drying occurs, fibrils deposit onto the tube. More slurry can be applied to the tube to add to matt thickness. When all fibrils have dried, the matt is removed as a seamless product from the tube. If reinforcement of the tubular matt is desired, fibers, bundles of fibers or fabrics can be positioned in the tube before or while the slurry is applied to the tube. These methods also apply to matts cast in other shapes, such as spheres, where the rolling would occur in more than one direction.

In a vascular prosthesis, the matt would become the inner layer inside of which the endothelial cells would be seeded. A single density foam would be cast around the matt for the albumenal substrate for the smooth muscle cells and adventitial fibroblasts.

Ligament implants, as multifilament forms of the biopolymers of the invention, can be enhanced with the matt, matt composites, and matt compositions of the invention to promote cell seeding. For example, continuous ligament multifilament structures can be produced with or without the addition of extracellular matrix particulates, to have selected characteristics. Ligament cells can then be delivered to the ligament which can be embedded in a matt casing. The ligament can then be mounted in a tubular tissue maturation chamber. After the ligament cells have attached to the ligament, the ligament is subjected to a regime of cyclical axial elongation resulting in stress, which is increased in magnitude as the ligament matures. The mature biopolymer ligaments can be used, for example, as ligament prostheses.

Dental implants can be formed from the matt, matt composites, and matt compositions of the invention. For example, the matt, matt composites, and matt compositions can be prepared as specialized dental implants for periodontal ligament repair and bone rebuilding. In one embodiment, the matt, matt composites, and matt compositions of the invention are prepared as apron shaped implants which can be fixed to a tooth by tying the strings of the apron around the tooth. In another embodiment, the matt, matt composites, and matt compositions are designed as covers of post extraction sockets filled with bone replacement material or collagen composition. In yet another embodiment, the matt, matt composites, and matt compositions are designed as bone replacement material-filled tubes to serve as alveolar ridge builders.

The apron shaped matt, which can be produced as a matt with low porosity or a matt composition including a double density or quadruple density foam, i.e., a double density foam folded over on itself, for promoting periodontal ligament repair and bone rebuilding can be positioned between a gum flap and the alveolar bone in the area requiring periodontal ligament repair and bone rebuilding. The matt can be designed to block invasion by junctional epithelium of the cleaned and planed tooth zone. Periodontal ligament cells can then migrate into the matt, matt composite, or matt composition, bind to the matt, matt composite, or matt composition, and secrete extracellular matrix products into the matt, matt composite, or matt composition. The matt, matt composite, or matt composition can also be invaded by capillary endothelial cells and immune cells which provide defense against microbial assault. By excluding epithelium and by stimulating periodontal ligament cells, the matt, matt composite, or matt composition can promote regeneration of periodontal ligament and alveolar bone. The apron shaped dental implants can also be modified to include a bone replacement material as described herein. In one embodiment, the material can be included in an outpocketing of the apron which can be placed on the eroded alveolar bone. The bone replacement material provides pathways for invading bone cells. The apron shaped dental implant can also include extracellular matrix particulates generated from dental tissues. These extracellular matrix particulates provide the appropriate growth factors, e.g., bone and ligament specific growth factors, for promoting periodontal ligament cell and bone cell growth into the implant.

Alternatively, the matt, matt composites, and matt compositions of the invention can be prepared as post extraction socket covers. The matt can be used to cover the socket filler material which is inserted into sockets of extracted teeth. These socket fillers promote bone regeneration within the socket which, at a minimum, provides a foundation for a metal, e.g., titanium, fixture and subsequent application of a crown. The titanium or other material fixture can be anchored in a socket immediately after an extraction with calcium phosphate bone replacement material reinforced and covered or "tented" with one of the matt, matt composites, or matt compositions described herein as an apron. The socket fillers can also include extracellular matrix particulates generated from bone tissue or dental papilla. These extracellular matrix particulates provide the appropriate growth factors, e.g., bone specific growth factors, for promoting bone cell growth into the implant. In addition, in instances where the bony foundation for dental implants composed of metal does not provide adequate support for the metal implant, bone replacement material reinforced or strengthened with the foams and foam compositions of the invention can be used to reinforce the bony foundation.

In yet another embodiment, the matt, matt composites, and matt compositions can be designed as alveolar ridge substitutes or alveolar ridge builders. Alveolar ridge substitutes are used to provide underpinning for dentures. Typically, the alveolar ridge substitutes are designed as biopolymer matt tubes of the appropriate length which are filled with non-resorbable calcium phosphate bone replacement material to build up a mineralized platform along the alveolar ridge and to promote development of bone and a connective tissue framework around the calcium phosphate particles. The alveolar ridge builders of the invention have the same design as that of the alveolar ridge substitutes except that the matt tube is filled with resorbable forms of bone replacement material to promote bone development. The composition of the alveolar ridge builders promotes bone cell and blood capillary penetration leading to regrowth and restoration of the ridge prior to, for example, installation of a denture or a metal implant. The matt tube of the alveolar ridge builder can also include extracellular matrix particulates which promote alveolar ridge bone regeneration.

Similarly, the matt, matt composites, and matt compositions of the invention enriched, for example, with extracellular matrix particulates derived from organs e.g., cardiac tissue, bladder tissue, tissue from the small intestine, lung tissue, pancreatic tissue, hepatic tissue, skin tissue, and other organ tissue, can be seeded with analogous organ cells such as those of the endocrine pancreas, e.g., pancreatic islet cells, or those of the liver, e.g., hepatocytes, as means of promoting cell proliferation before and/or after implantation so that after implantation and vascularization of the cell-laden matt implant, a functional replacement organ develops.

Examples of cell types which have been successfully grown in and on the matt and matt compositions of the invention include mesenchymal cells, dermal fibroblasts, keratinocytes, osteoblasts, gingival fibroblasts, and tendon and ligament cells.

Biopolymer matts are described more fully in Attorney Docket No. TSS-028, filed Mar. 17, 1998, the contents of which are herein incorporated by reference.

Fabrication of Collagen Fibers

A biopolymer construct can be fabricated from biopolymer fibers. Methods and apparatus for fabricating biopolymer fibers are known to those of ordinary skill in the art as disclosed in U.S. Pat. No. 5,562,946, entitled "Apparatus and Method for Spinning and Processing Collagen Fiber," issued Oct. 8, 1996, and herein incorporated by reference.

It will thus be seen that the invention efficiently attains the objects set forth above, among those made apparent from the preceding description. Generally, disclosed herein are methods for exposing a biopolymer replacement tissue to a culturing, or maturation fluid, and for applying selected forces and/or stresses to the exposed tissue. Forces may be transmitted to the tissue by the maturation fluid. The invention functions in part by conditioning tissue in vitro in a manner designed to simulate selected in vivo conditions, i.e., the conditions under which a tissue grows, i.e., exposed to certain fluids, such as synovial fluid, and subjected to certain stresses, such as shear stresses.

Techniques disclosed herein include mounting a replacement tissue such that a surface of the tissue is spaced by a selected gap from a second surface, providing a maturation fluid in the gap for contacting at least a portion of each of the surfaces, and moving one of the surfaces relative to the other. Pressing the surfaces together subjects the tissue to a compressive pressure, which can be provided with or without relative motion between the surfaces. Tissue surfaces can slidingly and frictionally engage, or can frictionally and non-slidingly engage. Several embodiments of apparatus are disclosed for implementing the above techniques. However, these embodiments are intended as illustrative of apparatus for practicing the present invention and not as limiting. One of ordinary skill of the art, with knowledge of the present disclosure, can likely envision other embodiments, or variations of the disclosed embodiments, that encompass, and accomplish the purposes of, the present invention. For example, one of ordinary skill in the art could couple the transverse piston 154 in FIG. 2A to an electromechanical actuator, rather than have the transverse piston 154 driven by fluid pressure. Accordingly, these variations and embodiments are considered within the spirit and scope of the invention.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

1. An apparatus for maturing biopolymer tissue, comprising first support means having a first surface for receiving and mounting a biopolymer tissue having a first tissue surface, second support means having a second surface facing said first tissue surface, fluid means for introducing a maturation fluid to one of said first tissue surface and said second surface, and relative motion means coupled to at least one of said first and second support means for providing relative motion between the tissue received and mounted by said first surface and said second surface for subjecting the tissue to selected forces.

2. The apparatus of claim 1, wherein said fluid means includes means for maintaining the maturation fluid in communication with the biopolymer tissue received and mounted by said first surface.

3. The apparatus of claim 1, wherein said fluid means includes a fluid reservoir adapted for receiving and confining maturation fluid and for immersing at least a portion of the biopolymer tissue received and mounted by said first surface in the maturation fluid.

4. The apparatus of claim 1, wherein said fluid means includes nozzle means for directing a flow of maturation fluid towards the biopolymer tissue and said second surface.

5. The apparatus of claim 1, wherein said second support means is adapted for receiving and mounting a second biopolymer tissue.

6. The apparatus of claim 1, wherein said relative motion means includes means for translating the first tissue surface of biopolymer tissue received and mounted by said first surface of said first support means relative to said second surface of said second support means at speeds ranging between about 0.5 cm/sec and about 50 cm/sec.

7. The apparatus of claim 1, wherein said second surface of said second support means is spaced along a first axis from said first tissue surface of said first tissue received and mounted by said first support means, and wherein said relative motion means comprises means for translating, in a plane substantially transverse to said first axis, the first tissue surface relative to said second surface at speeds ranging between about 0.5 cm/sec and about 50 cm/sec.

8. The apparatus of claim 1, wherein at least one of said first and second support means includes a block forming one of said first and second surfaces, and wherein said relative motion means comprises a linear electromechanical actuator coupled to said block to cyclically translate said block in a plane substantially parallel to one of said first and second surfaces.

9. The apparatus of claim 1, wherein at least one of said first and second support includes means forming a bore in said housing, said bore mounting a piston for translation therein, and said relative motion means includes means forming fluid ports in communication with said bore and means for introducing a fluid to said bore via said fluid ports so as to translate said piston in said bore.

10. The apparatus of claim 1, wherein one of said first and second support means includes an inner rotatable cylinder and the other includes an outer hemi-cylinder, and said relative motion means includes means for rotating said rotatable cylinder.

11. The apparatus of claim 1, further including spacing means for spacing the first tissue surface of the biopolymer tissue received and mounted on said first surface from said second surface of said second support means by a selected gap.

12. The apparatus of claim 11, wherein said spacing means varies said gap between first tissue surface of the biopolymer tissue received and mounted on said first surface and said second surface by between about 0 mm and about 5 mm.

13. The apparatus of claim 11, wherein said spacing means includes an adjustment stage coupled to at least one of said first and second support means.

14. The apparatus of claim 11, wherein at least one of said first and second support means includes a piston disposed for translation in a bore, and said spacing means includes means forming fluid ports in said bore and means for varying the volume of a fluid in said bore, via said fluid ports, so as to translate said piston in said bore.

15. The apparatus of claim 1, further comprising compression means for subjecting at least the biopolymer tissue received and mounted by said first surface to a selected compressive pressure.

16. The apparatus of claim 15, wherein said compression means is adapted for generating a compressive pressure on the biopolymer tissue received and mounted on said first surface of said first support means of between about 0 psi and about 100 psi.

17. The apparatus of claim 15, wherein said compression means includes means for compressing the biopolymer tissue mounted on said first surface of said first support means and said second support means together.

18. The apparatus of claim 17, wherein said compression means further comprises platform means adapted for receiving a weight, said platform means coupled to at least one of said first and second support means for transmitting at least a portion of the gravitational force on the weight to said support means coupled thereto.

19. The apparatus of claim 17, wherein at least one of said first and second support means includes a piston disposed for travel in a bore having means forming at least one fluid port therein, and said compression means includes means for providing, via said fluid ports, a fluid to said bore such that said fluid has a selected pressure in said bore.

20. The apparatus of claim 5, further comprising compression means for compressively engaging the biopolymer tissue received and mounted by said first surface with the biopolymer tissue received and mounted by said second surface of said second support means such that a compressive pressure of between about 0 psi and about 100 psi acts on each of the biopolymer tissues.

21. The apparatus of claim 1, wherein the maturation fluid comprises a thixotropic fluid for transmitting shear forces between biopolymer tissue mounted and received on said first surface and said second surface.

22. The apparatus of claim 1, wherein the biopolymer tissue mounted on said first surface comprises a biopolymer foam.

23. The apparatus of claim 22, wherein said first support means is adapted for interposing bone cement between said first surface and the biopolymer tissue received and mounted thereon.

24. The apparatus of claim 23, wherein said bone cement comprises calcium phosphate.

25. The apparatus of claim 1, further including
housing means for confining a fluid, said housing means having
   means forming a first bore having first and second ends and extending along a first longitudinal axis,
   means forming a second bore having first and second ends and extending along a second longitudinal axis disposed at an angle relative to said first longitudinal axis, said second bore intersecting, at the second end thereof, said first bore between said first and second ends thereof,
wherein said first support means includes an extended piston disposed for translation in said first bore, said piston having an extended piston first face, an extended piston second face, and an interconnecting section therebetween, said interconnecting section having an outer surface, and
wherein said second support means including a transverse piston disposed in said second piston bore, said transverse piston having a transverse piston first face and a transverse piston second face.

26. The apparatus of claim 25, wherein said transverse piston second face is adapted for forming said second surface of said second support means, and said outer surface of said interconnecting section is adapted for forming at least a portion of said first surface of said first support means so as to face said transverse piston second face.

27. The apparatus of claim 26, further including compression means for applying a selected compressive force to at least the biopolymer tissue mounted and received on said first surface.

28. The apparatus of claim 26, further including spacing means for translating said transverse piston in said second bore to vary the spacing between the first tissue surface of the biopolymer tissue received and mounted on said first surface and said second surface.

29. The apparatus of claim 26, wherein said extended piston divides said first bore into a first volume bounded in part by said extended piston first face and said first end of said first bore, and a second volume bounded in part by said extended piston second piston face and said second end of said first bore.

30. The apparatus of claim 29, wherein said relative motion means includes means forming fluid ports in said first piston bore for transferring a fluid into one of said first and second volumes, and means for providing and for controlling the transfer of said fluid into said first and second volumes for selectively translating said extended piston in said first bore.

31. The apparatus of claim 29, wherein said first and second bores intersect so as to define a third volume bounded in part by said outer surface of said interconnecting section of said extended piston and said transverse piston second face, and said transverse piston divides said second bore into a fourth volume bounded in part by said first end of said second bore and said first face of said transverse piston, said apparatus further including means forming a fluid port in said second bore for transferring fluid into said fourth volume.

32. The apparatus of claim 31, further including means for controlling the transfer of a fluid to said fourth volume for adjusting said spacing between the biopolymer tissue received and mounted by said first surface and said second surface.

33. The apparatus of claim 31, further including compression means for engaging the biopolymer tissue received and mounted by said first surface and said second surface for applying a selected compressive pressure to at least the biopolymer tissue received and mounted by said first surface, said compression means including means for providing and transferring a fluid to said fourth volume so as to provide a selected fluid pressure in said fourth volume.

34. The apparatus of claim 31, wherein said means for introducing a maturation fluid includes means for transferring fluid between said third volume and at least one of said first, second and fourth volumes.

35. Apparatus for developing cartilage tissue, comprising
a fluid reservoir for holding a maturation fluid,
a first support element adapted for mounting a first biopolymer tissue having a first tissue surface,
a second support element adapted for mounting a second biopolymer tissue having a second tissue surface facing the first tissue surface of the first biopolymer tissue,
said first and second support elements being adapted for immersing at least a portion of said first and second biopolymer tissue in the maturation fluid so as to contact the first and second biopolymer tissue surfaces, and
translation means for translating said first support element relative to said second support element to translate said first tissue surface relative to said second tissue surface so as to develop the tissue.

36. The apparatus of claim 35, wherein said translation means comprises an electromechanical actuator coupled to said first support element.

37. The apparatus of claim 35, wherein said electromechanical actuator linearly reciprocates said first support element.

38. The apparatus of claim 35, further comprising compression means coupled to at least one of said first and second support elements for pressing together the first and second biopolymer tissue.

39. The apparatus of claim 35 wherein said first tissue surface is spaced from said second tissue surface so as to form a gap therebetween.

40. The apparatus of claim 39, further comprising variable spacing means for varying the spacing between the first and second biopolymer tissue.

41. Apparatus for promoting development of a biopolymer tissue, comprising
a reservoir for confining a maturation fluid,
a rotatable inner support cylinder having an outer circumferential surface adapted for mounting a first biopolymer tissue having an outwardly facing tissue surface,
an arcuate support element spaced from said support cylinder and having an inner mounting surface adapted for mounting a second biopolymer tissue having an inwardly facing tissue surface,
said rotatable support cylinder and said arcuate support element being spaced apart such that the outwardly facing tissue surface is spaced from and faces the inwardly facing tissue surface to form a gap therebetween, said rotatable support cylinder and said hemi-cylindrical support element being operatively arranged with said reservoir such that the maturation fluid held therein is introduced to said gap and contacts at least a portion of each of the inwardly and outwardly facing tissue surfaces, and
rotating means for rotating said rotatable inner support cylinder.

42. The apparatus of claim 41, wherein the outwardly facing tissue surface is spaced from the second inwardly facing tissue surface by between about 0 mm and about 5 mm.

43. The apparatus of claim 41, further comprising compression means for compressing together the inwardly and outwardly facing tissue surfaces.

44. The apparatus of claim 41, wherein said rotatable inner support cylinder and said arcuate support element are coaxially mounted.

45. The apparatus of claim 41, wherein said rotatable support cylinder and said arcuate support element are coaxially mounted and said gap is uniform.

46. The apparatus of claim 41 wherein said rotation means includes an electric motor having a shaft coupled to said rotatable cylinder.

47. Apparatus for the maturation of biopolymer tissue, comprising
 a housing having
  means forming a first bore having first and second ends and extending along a first longitudinal axis,
  means forming a second bore having a first and second ends and extending along a second longitudinal axis disposed at an angle to said first longitudinal axis, said second bore intersecting, at the second end thereof, said first bore between said first and second ends thereof,
 an extended piston disposed for translation in said first bore, said extended piston having an extended piston first face, an extended piston second face, and an interconnecting section therebetween, said interconnecting section having an outer surface adapted for receiving and mounting a first biopolymer tissue having a first tissue surface, and
 a transverse piston disposed for translation in said second bore, said transverse piston having a transverse piston first face and a transverse piston second face, said second face being disposed for receiving and mounting a second biopolymer tissue having a second tissue surface facing the first tissue surface.

48. The apparatus of claim 47, wherein said extended piston divides said first bore into a first volume, bounded in part by said extended piston first face and said first end of said first bore, a second volume, bounded in part by said extended piston second piston face and said second end of said first bore.

49. The apparatus of claim 48, wherein said first and second bores intersect and define a third volume bounded in part by said outer surface of said interconnecting section of said extended piston and said transverse piston second face.

50. The apparatus of claim 49, wherein said transverse piston divides said second bore into a fourth volume bounded in part by said first end of said second bore and said first face of said transverse piston.

51. The apparatus of claim 50, further comprising means forming at least one fluid port in said first bore for transferring a first fluid to one of said first and second volumes.

52. The apparatus of claim 51, further comprising means forming at least one fluid port in said second bore for transferring a second fluid to said fourth volume.

53. The apparatus of claim 52, further comprising means for transferring fluid between said third volume and at least one of said first, second and fourth volumes.

54. The apparatus of claim 51, further comprising means for controlling the transfer of the first fluid to said first and second volumes for selectively translating said extended piston in said first bore.

55. The apparatus of claim 52, further comprising means for controlling the transfer of the second fluid to said fourth volume for selectively spacing the first biopolymer tissue from the second biopolymer tissue so as to form a selected gap between the first tissue surface and the second tissue surface.

56. The apparatus of claim 52, further comprising means for controlling the transfer of the second fluid to said fourth volume for selectively pressing the first biopolymer tissue against the second biopolymer tissue for providing a selected compressive pressure on at least one of the first and second biopolymer tissue.

57. A method of maturing biopolymer tissue, comprising the steps of
 mounting a first biopolymer tissue having a first tissue surface to a first surface of a first support structure,
 providing a second support structure having a second surface,
 arranging said first and second support structures such that the second surface and the first tissue surface face each other,
 introducing a maturation fluid to contact at least a portion of the second surface and at least a portion of the first tissue surface,
 translating at least one of said first and second support structures relative to the other for applying selected forces, via the maturation fluid, to the first tissue.

58. The method of claim 57 further including the step of spacing the second surface of the second support structure from the first tissue surface of the first tissue mounted on the first support structure to form a gap between the said surfaces.

59. The method of claim 56, wherein the step of introducing a maturation fluid includes introducing the maturation fluid to the gap and includes the steps of providing a reservoir confining the maturation fluid and immersing at least a portion of the first biopolymer tissue and a portion of the second surface in the maturation fluid.

60. The method of claim 57, wherein the step of introducing a maturation fluid further comprises the step of introducing a thixotropic fluid.

61. The method of claim 57, wherein the step of introducing a maturation fluid further comprises the step of introducing hyaluronic acid.

62. The method of claim 57, wherein the step of introducing a maturation fluid further comprises the step of introducing synovial fluid.

63. The method of claim 58, wherein the step of spacing further comprises the step of separating the second surface and the first sheet of tissue such that at least a portion of the first tissue and at least a portion of the second surface are separated by a distance from between about 0 mm and about 5 mm.

64. The method of claim 57, wherein the step of translating further comprises the step of moving the first sheet of tissue relative to the second surface at speeds between about 0.5 cm/sec and about 50 cm/sec.

65. The method of claim 57, wherein the step of translating further comprises the step of linearly reciprocating the first biopolymer tissue relative to the second surface.

66. The method of claim 57, wherein the step of translating further comprises the step of rotating said first support structure relative to said second support structure.

67. The method of claim 57, further comprising the step of applying a selected compressive force to at least the first biopolymer tissue.

68. The method of claim 67, wherein the step of applying selected compressive forces further comprises the step of reducing the gap so as to press the second surface of said second support structure against the first biopolymer tissue.

69. The method of claim 57, further comprising the step of mounting a second biopolymer tissue on the second support structure such that the second sheet of biopolymer tissue has a surface forming the second surface.

70. Apparatus for the maturation of biopolymer tissue, comprising an inner cylinder extending longitudinally along a central axis and having an outer surface for receiving and mounting a first biopolymer tissue having an outwardly facing tissue surface, an outer cylinder having a lumen therethrough and extendingly longitudinally along a second central axis substantially parallel to said first central axis, said outer cylinder having an outer wall having an inner face bounding said lumen, said inner face for receiving and mounting a second biopolymer tissue having an inwardly facing tissue surface, said inner cylinder being disposed within said lumen such that said inwardly facing and outwardly facing tissue surfaces face each other, means for providing a maturation fluid within said lumen for contacting said inwardly and outwardly facing tissue surfaces, and at least a first rotational drive means for rotating at least one of said inner and outer cylinders for providing relative motion between said inwardly facing and outwardly facing tissue surfaces.

71. The apparatus of claim 70 wherein said inwardly facing tissue surface is spaced from said outwardly facing tissue surface by a gap.

72. The apparatus of claim 71 wherein the radius of curvature of the outer surface of said inner cylinder is less than the radius of curvature of said inner face of said outer wall of said outer cylinder and said inwardly facing tissue surface is spaced from said outwardly facing tissue surface by a non-uniform gap, said gap having a minimum magnitude and a maximum magnitude at points about the circumference of said tissue surfaces.

73. The apparatus of claim 71 including spacing means for varying the magnitude of said gap, said spacing means including means for varying the offset, in a direction transverse to said central axes, between said central axes of said cylinders.

74. The apparatus of claim 70 wherein said inwardly facing tissue surface engages said outwardly facing tissue surface at least along a line of engagement substantially parallel to said central axes.

75. The apparatus of claim 74 including a rotational support means for rotationally supporting the second of said inner and outer cylinders, such that rotationally driving one of said cylinders with said rotational drive means rotates the other of said cylinders due to frictional contact of said tissue surfaces at least along said line of engagement therebetween.

76. The apparatus of claim 74 including a second rotational drive means for rotationally driving the other of said cylinders such that said tissue surfaces frictionally and slidingly engage at least along said line of engagement.

77. The apparatus of claim 70 including means for compressing said outwardly facing tissue surface against said inwardly facing tissue surface at least along a line of engagement between said tissue surfaces.

78. The apparatus of claim 70 including translation means for translating said inner and outer cylinders relative to each other to vary the offset between said central axes in a plane transverse to said central axes such that a line of engagement of said inwardly and outwardly facing tissue surfaces is circumferentially varied about the inwardly facing tissue surface.

79. The apparatus of claim 78 wherein said inner cylinder is mounted to a shaft for rotation about said central axis of said inner cylinder, said rotational drive means including said translations means, said translation means including means for translating said shaft, and wherein frictional contact between said inwardly and outwardly facing tissue surfaces along said line of engagement rotates said inner cylinder about said first central axis.

80. An apparatus for maturing biopolymer tissue, comprising a housing having an inner chamber, an applicator having an arcuate pressure applying surface and adapted to be movable within the inner chamber, first support means having a first surface for receiving and mounting a biopolymer tissue having a first tissue surface, said first surface having a concave surface feature formed therein, and means for introducing a maturation fluid to the inner chamber, whereby said applicator is movable relative to the tissue to apply a force thereto in the presence of the maturation fluid to mature the tissue.

81. The apparatus of claim 80 further comprising means for rotating said applicator.

82. The apparatus of claim 80 further comprising means for placing said applicator in contact with the tissue.

83. The apparatus of claim 80, wherein said first support means comprises a piston cup assembly mounted within the housing chamber.

84. The apparatus of claim 83, wherein said piston cup assembly further comprises one or more perfusion channels formed therein.

85. The apparatus of claim 84, wherein said piston cup divides said inner chamber into an input chamber and an output chamber, said perfusion channels allowing fluid to pass between said input and output chambers, said apparatus further comprising sealing means for preventing fluid leakage about said piston cup and between said input and output chambers.

86. The apparatus of claim 84, wherein said applicator has provided thereon a flange, said apparatus further comprising a stop ring mounted within said inner chamber of said housing, said stop ring having a flange adapted for engagement with the flange of said applicator to define a selected position of said applicator.

* * * * *